US010378056B2

(12) United States Patent
Kertai et al.

(10) Patent No.: US 10,378,056 B2
(45) Date of Patent: Aug. 13, 2019

(54) COMPOSITIONS AND METHODS FOR IDENTIFYING ALTERED EFFECTIVENESS OF BETA BLOCKER THERAPY

(71) Applicant: Duke University, Durham, NC (US)

(72) Inventors: Miklos D. Kertai, Chapel Hill, NC (US); Mihai V. Podgoreanu, Chapel Hill, NC (US); Joseph P. Mathew, Durham, NC (US); Yi-Ju Li, Durham, NC (US)

(73) Assignee: Duke University, Durham, NC (US)

( * ) Notice: Subject to any disclaimer, the term of this patent is extended or adjusted under 35 U.S.C. 154(b) by 230 days.

(21) Appl. No.: 15/198,473

(22) Filed: Jun. 30, 2016

(65) Prior Publication Data

US 2017/0002417 A1     Jan. 5, 2017

Related U.S. Application Data

(60) Provisional application No. 62/188,232, filed on Jul. 2, 2015.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

PUBLICATIONS

Kertai (Circ Cardiovasc Genet. 2014;7:625-633 published online Jul. 21, 2014).*
Mayson (Cardiology in Review vol. 15 No. 5 Sep./Oct. 2007 pp. 231-241).*
Fox (PloS One Sep. 2011 vol. 6 Issue 9 e24593 pp. 1-9).*
Kertai (American Heart Journal vol. 170, Issue 3, Sep. 2015, pp. 580-590.e28).*
Bartels et al. "Apolipoprotein epsilon 4 genotype is associated with less improvement in cognitive function five years after cardiac surgery: a retrospective cohort study" *Canadian Journal of Anesthesia* 62(6):618-626 (2015).
Kertai et al. "Pharmacogenomics of Beta-Blockers and Statins: Possible Implications for Perioperative Cardiac Complications" *Cardiothoracic and Vascular Anesthesia* 26(6):1101-1114 (2012).
Kertai et al. "G Protein-Coupled Receptor Kinase 5 Gene Polymorphisms are Associated With Postoperative Atrial Fibrillation After Coronary Artery Bypass Grafting in Patients Receiving β-Blockers" *Circulation: Cardiovascular Genetics* 7:625-633 (2014).
Kertai et al. "Genome-wide association study of new-onset arterial fibrillation after coronary artery bypass grafting surgery" *American Heart Journal* 170:580-590.e28 (2015).
Kertai et al. "Genome-wide association study of perioperative myocardial infarction after coronary artery bypass surgery" *BMJ Open* 5:e006920 (2015).
Kertai et al. "Gene signatures of postoperative atrial fibrillation in atrial tissue after coronary artery bypass grafting surgery in patients receiving β-blockers" *Journal of Molecular and Cellular Cardiology* 92:109-115 (2016).
Kertai et al. "Interleukin-1β gene variants are associated with QTc interval prolongation following cardiac surgery: a prospective observational study" *Canadian Journal of Anesthesia* 63(4):397-410 (2016).
Lymperopoulos et al. "GRK2 Inhibition in Heart Failure: Something Old, Something New" *Current Pharmaceutical Design* 18(2):186-191 (2012) (Abstract Only).
Stafford-Smith et al. "Genome-wide association study of acute kidney injury after coronary bypass graft surgery identifies susceptibility loci" *Kidney International* 88(4):823-832 (2015).

* cited by examiner

*Primary Examiner* — Amanda Haney
(74) *Attorney, Agent, or Firm* — Myers Bigel, P.A.

(57) ABSTRACT

The present invention provides a method of identifying a human subject as having an increased risk of altered effectiveness of beta blocker therapy, comprising detecting in the subject one or more single nucleotide polymorphism associated with increased risk of altered effectiveness of beta blocker therapy.

10 Claims, No Drawings

Specification includes a Sequence Listing.

SEQUENCE LISTING

<160> NUMBER OF SEQ ID NOS: 16

<210> SEQ ID NO 1
<211> LENGTH: 51
<212> TYPE: DNA
<213> ORGANISM: Homo sapiens

<400> SEQUENCE: 1
gcttactttc tctagtttgc agtttmtttg tgtataaact ggagacacta a     51

<210> SEQ ID NO 2
<211> LENGTH: 30
<212> TYPE: DNA

<213> ORGANISM: Homo sapiens

<400> SEQUENCE: 2
aagtagctta ctttctctag tttgcagttt                               30

<210> SEQ ID NO 3
<211> LENGTH: 30
<212> TYPE: DNA
<213> ORGANISM: Homo sapiens

<400> SEQUENCE: 3
tttgtgtata aactggagac actaacacca                               30

<210> SEQ ID NO 4
<211> LENGTH: 1001
<212> TYPE: DNA
<213> ORGANISM: Homo sapiens

<400> SEQUENCE: 4
gagtctcact ctgtccccca ggctggagtg cagtggtgta atcttggctc attgcaacct    60
ctgcctccca gattcaagca attcttctgc ctcagtctcc caagtagctg ggactacagg   120
tacctgccac cacgcctagc taattttgtg tttttagtag agacagggtt tcaccatgtt   180
ggccaggctg gtctcgaact cctgacctca tgtgatccac ctgccttggc ctccccaagt   240
gctgggatta caggcgtgag ccactgcgcc cagcctgcgc atgttcttta aaccagacac   300
tggctaacag atacttgtta agctcctcct ctgtgctagg cattgctgca gtcaccggac   360
ttgtgtcaca ggccacccct gtccagcagc gagggctcct ggaaggatct ctgtcactgt   420
catcaagatg aagtggtggt gctgctgctg ccagccctgt gactttgagc aagtagctta   480
ctttctctag tttgcagttt mtttgtgtat aaactggaga cactaacacc aacctggtag   540
agcctctggg aaggccagca gagtgttgca cacaggccat cattgtcatc agcatcgtca   600
ttgtcatcgt catcctcacg gcgatagtgg tttgagggca gaggttgagg acccttttgag   660
agggttttgg agtttcccag agaagctgaa tcggctacac atgatggatg aggccagctg   720
tttttgtgct gaggtgaagt gggttcagtg tcccagagac tgttgccttg gagtcatcgg   780
aatcctcctc ttcctagagc actgcctcca gcttcctctt cttggaagcc tgccctgatt   840
cctgcagtcc tcagccttcc ttcctcccca cggctccaca gtttgcccag ggaagctgga   900
agcatcacac tctgcccagg cccctgctct ggcccagtgt gtttccttga aaggacgtgt   960
gtcatctaga agcctgcagc cccgagtcct aacaatggtt a                     1001

<210> SEQ ID NO 5
<211> LENGTH: 51
<212> TYPE: DNA
<213> ORGANISM: Homo sapiens

<400> SEQUENCE: 5
gactatcatc ttccttgccc agacakcaga tatcatttaa aatggaaacc t           51

<210> SEQ ID NO 6
<211> LENGTH: 30
<212> TYPE: DNA
<213> ORGANISM: Homo sapiens

<400> SEQUENCE: 6
gcctcgacta tcatcttcct tgcccagaca                               30

<210> SEQ ID NO 7
<211> LENGTH: 30
<212> TYPE: DNA
<213> ORGANISM: Homo sapiens

<400> SEQUENCE: 7
cagatatcat ttaaaatgga aacctgtggg                               30

<210> SEQ ID NO 8
<211> LENGTH: 1001
<212> TYPE: DNA
<213> ORGANISM: Homo sapiens

<400> SEQUENCE: 8
tttttgagac agagtctcac tccgtcaccc attctggagt gcagtgatgc agtctcactc    60
actgcaaccc ccgcctcctg ggttcaaatg attctcatgc ctcagcctcc caagtagctg   120
ggattacagg tgtgcgccac cacgcccagc taaattttgt attttttaata gagacagggc  180 tttgccatat tggccaggct ggtcttgaac tcttggcctc aagtaatctg cccacctcag   240
cctcccaaag tggctgggat tacaggtgtc agccaccatg cccagcccca aaacttactt   300
ttaattcctt ttctcattac aaaaataata tatgtcaatg gttgcaattt ccaaaacaat   360
tttaaaaggg gaaaataaaa actgccaatg agataaggat aaacactgtt aacactttgg   420
tctgttgccc ttttgtagtt tgttctgctt ctagggagag aattgtacca gcctcgacta   480
tcatcttcct tgcccagaca kcagatatca tttaaaatgg aaacctgtgg gttgtagaat   540
cccccttgga ctgggaggca gaagacccag tttcttgtgt taccacttgg tcctgtggcc   600 tgggaaagc cacttaacct tgatttgctc gtctttaaaa tggggactca gtattcctca   660
ccttagcaga tggagtggcc aaaggtgttt ctggcagaga gtgctttgca aagtgctgtg   720
caaattgctg gccagttttg atgtgggtgt gtgagccttt ggttggacaa atggccagag   780
tagttttcct gtcttcttgg gggaactgtg acccttctc gtaaagctgt tctgtctctg    840
atcctggtga acatcaccag cttcctctag ctgcccagag ctgcccctcc cctctgccct   900
gccgtgtggc acctggccca gtgcagtgtc cagtccctct ccaggtcccg atgcctcggc   960
ctccacagta tctcctagtc tgcccctctc gccccatctc c                     1001

<210> SEQ ID NO 9
<211> LENGTH: 51
<212> TYPE: DNA
<213> ORGANISM: Homo sapiens

<400> SEQUENCE: 9
aagatgctgt ggatcgtttt gggaartaag caggcaatga ataagtcagt g             51

<210> SEQ ID NO 10
<211> LENGTH: 30
<212> TYPE: DNA
<213> ORGANISM: Homo sapiens

<400> SEQUENCE: 10
attggaagat gctgtggatc gttttgggaa                               30

<210> SEQ ID NO 11
<211> LENGTH: 30
<212> TYPE: DNA
<213> ORGANISM: Homo sapiens

<400> SEQUENCE: 11

```
taagcaggca atgaataagt cagtgcgtta                                             30

<210> SEQ ID NO 12
<211> LENGTH: 401
<212> TYPE: DNA
<213> ORGANISM: Homo sapiens

<400> SEQUENCE: 12
gcatccctct ttcttcaaac tgctgggaag cccatagctc agtttgatgt caaaagcaaa           60
gctctctttc atctgatgtc atcggggggag ctcatttgat tttcccctcc ctcttttgct         120
gtttgtttcc tgttctttgt cttttatgga acaattgaac atgtgccttt attggaagat         180
gctgtggatc gttttgggaa rtaagcaggc aatgaataag tcagtgcgtt agaaacgaag         240
gggagaagaa gctccctgct cggcctagga agcaggcagg tctgagcctt gttcctcctc         300
tctggagaat ggacatatgg gcacctgccc tgtagacctt gaggaatgag aacagaatgg         360
gttctggtgg tccagtgtgc tgggcagcaa tgggcatgtc c                             401

<210> SEQ ID NO 13
<211> LENGTH: 51
<212> TYPE: DNA
<213> ORGANISM: Homo sapiens

<400> SEQUENCE: 13
aagatgctgt ggatcgtttt gggaartaag caggcaatga ataagtcagt g                   51

<210> SEQ ID NO 14
<211> LENGTH: 30
<212> TYPE: DNA
<213> ORGANISM: Homo sapiens

<400> SEQUENCE: 14
acccatcatt tcctgagtct gatagaggag                                             30

<210> SEQ ID NO 15
<211> LENGTH: 30
<212> TYPE: DNA
<213> ORGANISM: Homo sapiens

<400> SEQUENCE: 15
taggatctgt ccagtggctg ctgtttctgt                                             30

<210> SEQ ID NO 16
<211> LENGTH: 1001
<212> TYPE: DNA
<213> ORGANISM: Homo sapiens

<400> SEQUENCE: 16
ggaagctggg ccgccctcac tgcctgtgtc ctcgccacct cctattggga aactctggtt           60
gccctccaag agtccacata ctgcaggctc ttaattaaga agtatgttc ccatttcatg          120 tcactcgaaa agaatgaaaa cagtgacagc atttatttat cttaactatc aatatcattc         180
ctgtttctca gtccgctggg ggtatgagtc ttgaaggaat tgactgggtt atgagatttg         240
aacctcgggc atgtgctggt gggacacatg tggcctgctt ccgagaagga gccttgaagg         300
aagagcaagc aggctggcat ggccctgccc tgccctgccc tcccggagct cagggccgaa         360
gggctcggtg acagtgggga actcctgcct gctttggtgc taatggagag tcaaggttcc         420 ttttttcacca gctacctcct atctcctttc tcagtcatcg gagaagtaaa acccatcatt         480
tcctgagtct gatagaggag rtaggatctg tccagtggct gctgtttctg tggcacctac         540
```

```
tgtgtgctga ggctgggcca ggtgctcaca tgcgttgttg ccaatccccg gcagcaacca    600
gctaactctg atggcctcag gtaaagggac ttgcccaaga ccacacagcc atccagagtt    660
gctccactgt ggagacacta ttgccatttg gagcagaata attatgtgtg gcagggagct    720
gtcctgtgca ttgtggggta tttagcacat ccctggcctc cacccactaa tcagtagtaa    780
cctcacagtt gtgataacac aaaatgtcta cagacattgc caaaatttcc cgctgctgaa    840
aacctctgag ctaggggatg gaggtaggat tcagacccaa gcctgtgctt gttcgccacc    900
ctgtgctagc tctgaagaag tcctcaccca agcaaggcaa ccctgcttgc ctttaggatc    960
caggcagcgt ggtagtgctt tggtgtttct gaactatgta c                       1001
```

COMPOSITIONS AND METHODS FOR IDENTIFYING ALTERED EFFECTIVENESS OF BETA BLOCKER THERAPY

PRIORITY STATEMENT

This application claims the benefit, under 35 U.S.C. § 119(e), of U.S. Provisional Application Ser. No. 62/188,232, filed Jul. 2, 2015, the entire contents of which are incorporated in their entirety herein.

STATEMENT OF GOVERNMENT SUPPORT

This invention was made with government support under Grant Nos. HL075273, HL092071, AG09663, HL054316, HL069081, HL096978, HL108280, HL109971, HL095987 and HL101621, awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5405-483_ST25.txt, 6,996 bytes in size, generated on Aug. 25, 2016 and filed via EFS-Web, is provided in lieu of a paper copy. This Sequence Listing is hereby incorporated by reference into the specification for its disclosures.

FIELD OF THE INVENTION

The present invention relates to biomarkers associated with increased risk of altered effectiveness of beta blocker therapy following heart surgery.

BACKGROUND OF THE INVENTION

Postoperative atrial fibrillation (AF) is the most common complication following coronary artery bypass grafting surgery (CABG), occurring in 25% to 40% of patients. Studies have indicated that postoperative AF is associated with an increased incidence of congestive heart failure, myocardial infarction, renal insufficiency, and neurological events, resulting in longer hospital stays and increased total cost of surgery. The additional healthcare costs related to postoperative AF exceed $10,000 per patient, translating to more than $1 billion each year in the United States alone.

Sympathetic activation or an exaggerated response to adrenergic stimulation is an important trigger for postoperative AF. Beta-blockers (BBs) are a mainstay in the prevention and treatment of postoperative AF; however, approximately 20% of patients undergoing CABG develop postoperative AF despite BB use.

The present invention provides methods and compositions for identifying a subject as having an increased risk of altered effectiveness of beta blocker therapy.

SUMMARY OF THE INVENTION

In one aspect, the present invention provides a method of identifying a human subject as having an increased risk of altered effectiveness of beta blocker therapy, comprising: a) obtaining a nucleic acid sample from a subject undergoing coronary artery bypass grafting surgery; b) detecting in the nucleic acid sample of the subject: 1) an A allele at single nucleotide polymorphism rs3740563; 2) an A allele at single nucleotide polymorphism rs4752292; 3) an A allele at single nucleotide polymorphism rs11198893; 4) an A allele at single nucleotide polymorphism rs10787959; or 5) any combination of (1) through (4) above, wherein detection of said allele(s) identifies the subject as having an increased risk of altered effectiveness of beta blocker therapy.

The present invention also provides a method of treating a subject to prevent/ameliorate postoperative atrial fibrillation during and/or after coronary artery bypass grafting surgery, comprising: a) obtaining a nucleic acid sample from a subject undergoing coronary artery bypass grafting surgery; b) detecting in the nucleic acid sample of the subject: 1) an A allele at single nucleotide polymorphism rs3740563; 2) an A allele at single nucleotide polymorphism rs4752292; 3) an A allele at single nucleotide polymorphism rs11198893; 4) an A allele at single nucleotide polymorphism rs10787959; or 5) any combination of (1) through (4) above, wherein detection of said allele(s) identifies the subject as having an increased risk of altered effectiveness of beta blocker therapy; and c) modifying treatment for the subject identified in (b) by using alternative prevention and/or treatment strategies such as administration of a nondihydropiridine calcium channel blocker, and/or by prophylactic administration of amiodarone.

The present invention further provides a method of personalizing prevention strategies and/or alternative treatment options for a subject undergoing coronary artery bypass grafting surgery, comprising: a) obtaining a nucleic acid sample from a subject undergoing coronary artery bypass grafting surgery; b) detecting in the nucleic acid sample of the subject: 1) an A allele at single nucleotide polymorphism rs3740563; 2) an A allele at single nucleotide polymorphism rs4752292; 3) an A allele at single nucleotide polymorphism rs11198893; 4) an A allele at single nucleotide polymorphism rs10787959; or 5) any combination of (1) through (4) above, wherein detection of said allele(s) identifies the subject as having an increased risk of altered effectiveness of beta blocker therapy; c) treating the subject undergoing coronary artery bypass grafting surgery by administering a nondihydropiridine calcium channel blocker, and/or by prophylactic administration of amiodarone if the subject is identified in step (b) as having an increased risk of altered effectiveness of beta blocker therapy by; and d) not treating the subject undergoing coronary artery bypass grafting surgery by administering a nondihydropiridine calcium channel blocker, and/or prophylactic administration of amiodarone if the subject is not identified in step (b) as having an increased risk of altered effectiveness of beta blocker therapy.

Further provided herein is a kit comprising one or more reagents for the detection of the alleles of this invention.

The foregoing objects, features and advantages of the present invention will become more apparent from the following description in connection with the accompanying drawings.

DETAILED DESCRIPTION OF THE INVENTION

For the purposes of promoting an understanding of the principles of the present invention, reference will now be made to particular embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the invention relates.

The present invention is based on the unexpected discovery that a human subject can be identified as having an increased risk of altered effectiveness of beta blocker therapy, and such information can be used in developing a personalized plan for treating and/or preventing postoperative atrial fibrillation that may develop in the subject as a result of having coronary artery bypass grafting surgery.

The present invention is based on the unexpected discovery of particular alleles of single nucleotide polymorphisms (SNPs) that are statistically associated with an increased risk of altered effectiveness of beta blocker therapy. There are numerous benefits of carrying out the methods of this invention to identify a subject as having an increased risk of altered effectiveness of beta blocker therapy, including but not limited to, identifying subjects who need or would benefit from a personalized plan for treating and/or preventing postoperative atrial fibrillation that may develop in the subject as a result of having coronary artery bypass grafting surgery.

Thus, in one aspect, the present invention provides a method of identifying a human subject as having an increased risk of altered effectiveness of beta blocker therapy, comprising: a) obtaining a nucleic acid sample from a subject undergoing coronary artery bypass grafting surgery; b) detecting in the nucleic acid sample of the subject: 1) an A allele at single nucleotide polymorphism rs3740563; 2) an A allele at single nucleotide polymorphism rs4752292; 3) an A allele at single nucleotide polymorphism rs11198893; 4) an A allele at single nucleotide polymorphism rs10787959; or 5) any combination of (1) through (4) above, wherein detection of said allele(s) identifies the subject as having an increased risk of altered effectiveness of beta blocker therapy.

The present invention also provides a method of treating a subject to prevent/ameliorate postoperative atrial fibrillation after coronary artery bypass grafting surgery, comprising: a) obtaining a nucleic acid sample from a subject undergoing coronary artery bypass grafting surgery; b) detecting in the nucleic acid sample of the subject: 1) an A allele at single nucleotide polymorphism rs3740563; 2) an A allele at single nucleotide polymorphism rs4752292; 3) an A allele at single nucleotide polymorphism rs11198893; 4) an A allele at single nucleotide polymorphism rs10787959; or 5) any combination of (1) through (4) above, wherein detection of said allele(s) identifies the subject as having an increased risk of altered effectiveness of beta blocker therapy; and c) modifying treatment for the subject identified in (b) by using alternative prevention and/or treatment strategies such as administration of a nondihydropiridine calcium channel blocker, and/or by prophylactic administration of amiodarone.

The present invention further provides a method of personalizing prevention strategies and/or alternative treatment options for a subject undergoing coronary artery bypass grafting surgery, comprising: a) obtaining a nucleic acid sample from a subject undergoing coronary artery bypass grafting surgery; b) detecting in the nucleic acid sample of the polymorphism rs11198893; 4) an A allele at single nucleotide polymorphism rs10787959; or 5) any combination of (1) through (4) above, wherein detection of said allele(s) identifies the subject as having an increased risk of altered effectiveness of beta blocker therapy; c) treating the subject undergoing coronary artery bypass grafting surgery by administering a nondihydropiridine calcium channel blocker, and/or by prophylactic administration of amiodarone if the subject is identified in step (b) as having an increased risk of altered effectiveness of beta blocker therapy by; and d) not treating the subject undergoing coronary artery bypass grafting surgery by administering a nondihydropiridine calcium channel blocker, and/or prophylactic administration of amiodarone if the subject is not identified in step (b) as having an increased risk of altered effectiveness of beta blocker therapy.

In some embodiments of the methods of this invention, the detecting step can consist of detecting an A allele at single nucleotide polymorphism rs3740563 and an A allele at rs4752292.

In some embodiments of the methods of this invention, the nondihydropiridine calcium channel blocker, and/or the amiodarone is administered to the subject preoperatively, perioperatively, and/or postoperatively in any combination. In some embodiments, the nondihydropiridine calcium channel blocker, and/or the amiodarone is only administered to the subject perioperatively and/or postoperatively.

In some embodiments of the methods of this invention, a beta blocker is administered to the subject preoperatively, perioperatively and/or postoperatively, in any combination.

In some embodiments, the nondihydropiridine calcium channel blocker, and/or the amiodarone is administered intravenously.

The following dosing information is available for amiodarone:

Usual Adult Dose for Arrhythmias: Initial dose (IV): 1000 mg over the first 24 hours of therapy, delivered by the following infusion regimen: 150 mg over the first 10 minutes (15 mg/min), followed by 360 mg over the next 6 hours (1 mg/min). Maintenance infusion: 540 mg over the remaining 18 hours (0.5 mg/min) Initial dose (PO): Loading doses of 800 to 1600 mg/day are required for 1 to 3 weeks (occasionally longer) until initial therapeutic response occurs. When adequate arrhythmia control is achieved, or if side effects become prominent, the dose should be reduced to 600 to 800 mg/day for one month and then to the maintenance dose, usually 400 mg/day. Some patients may require up to 600 mg/day Amiodarone may be administered as a single daily dose, or in patients with severe gastrointestinal intolerance, as a twice daily dose.

Usual Pediatric Dose for Supraventricular Tachycardia: Less than 1 month: Limited data available: oral loading dose: 10 to 20 mg/kg/day orally in 2 divided doses for 7 to 10 days; dosage should then be reduced to 5 to 10 mg/kg/day once daily and continued for 2 to 7 months; this protocol was used in 50 infants (less than 9 months of age) and neonates (as young as 1 day of life); intravenous loading dose: 5 mg/kg given over 60 minutes; Note: Bolus infusion rates should generally not exceed 0.25 mg/kg/minute unless clinically indicated; most studies used bolus infusion time of 60 minutes to avoid hypotension; may repeat initial loading dose to a maximum total initial load: 10 mg/kg; do not exceed total daily bolus of 15 mg/kg/day. Less than 1 year: Initial dose: 600 to 800 mg/1.73 m$^2$/day orally for 4 to 14 days given in 1 to 2 divided doses/day. Maintenance dose: 200 to 400 mg/1.73 m$^2$/day orally given once a day. Greater than 1 year: Initial dose: 10 to 15 mg/kg/day orally for 4 to 14 days given in 1 to 2 divided doses/day. Maintenance dose: 5 to 10 mg/kg/day orally given once a day.

Nonlimiting examples of a nondihydropiridine calcium channel blocker include Diltiazem (Cardiazem®, Cartia®, Dilacor®, Dilt-CD®, Diltzac®, Taztia XT®, Tiamate®, Tiazac®).

A nonlimiting example of a prophylactic regimen for Diltiazem is 0.25 mg/kg intravenous loading dose over 2 min, then 5-15 mg/h intravenous continuous infusion.

In further aspects, the present invention provides a kit for carrying out the methods of this invention, wherein the kit can comprise oligonucleotides (e.g., primers, probes, primer/probe sets, etc.), reagents, buffers, etc., as would be known in the art, for the detection of the polymorphisms and/or alleles of this invention in a nucleic acid sample. For example, a primer or probe can comprise a contiguous nucleotide sequence that is complementary (e.g., fully (100%) complementary or partially (50%, 60%, 70%, 80%, 90%, 95%, etc.) complementary) to a region comprising an allele of this invention. In particular embodiments, a kit of this invention will comprise primers and probes that allow for the specific detection of the alleles of this invention. Such a kit can further comprise blocking probes, labeling reagents, blocking agents, restriction enzymes, antibodies, sampling devices, positive and negative controls, etc., as would be well known to those of ordinary skill in the art.

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. A subject of this invention can be any subject that is susceptible to atrial fibrillation and in particular embodiments, the subject of this invention is a human subject.

A "subject in need thereof" or "a subject in need of" is a subject known to have, or is suspected of having or developing cardiac surgery-associated atrial fibrillation or is at risk of having or developing cardiac surgery-associated atrial fibrillation as described herein. In particular embodiments, the subject is in need of, is scheduled for and/or is planning to undergo cardiac surgery (e.g., surgery to treat a cardiac disorder or coronary artery bypass grafting surgery).

For example, in particular embodiments, a subject identified by the methods of this invention as having an increased risk of altered effectiveness of beta blocker therapy can be administered a nondihydropiridine calcium channel blocker and/or amiodarone prior to surgery (e.g., prophylactically) to prevent cardiac surgery-associated atrial fibrillation. A subject of this invention can also be administered a nondihydropiridine calcium channel blocker and/or amiodarone during and/or following cardiac surgery to prevent or treat cardiac surgery-associated atrial fibrillation.

As used herein, "altered effectiveness of beta blocker therapy" means that beta-blockers despite their adequate dosage of administration do not provide the expected therapeutic benefit for the prevention of AF.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). In the methods of this invention, a nondihydropiridine calcium channel blocker and/or amiodarone may be administered alone and/or simultaneously with one or more other compounds. In some embodiments, the nondihydropiridine calcium channel blocker, and/or amiodarone may be administered sequentially, in any order. It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

As used herein, the term "ameliorate" refers to the ability to make better, or more tolerable, a condition such as cardiac-surgery-associated atrial fibrillation. In some embodiments, the term "prevent" refers to the ability to keep a condition such as cardiac-surgery-associated atrial fibrillation from happening or existing as well as to diminish or delay onset. In some embodiments, the term "treating" refers to the caring for, or dealing with, a condition such as cardiac-surgery-associated atrial fibrillation either medically or surgically.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

In some embodiments, a unique form of parenteral administration is via direct access to the coronary circulation, added to cardioplegia solutions routinely used during cardiac surgery. Such delivery can follow an antegrade route (via the aortic root into the coronary arteries) and/or a retrograde route (via the coronary sinus, great heart vein).

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

In addition to the nondihydropiridine calcium channel blocker and/or amiodarone provided herein, a composition of the present invention (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

Excipients such as diluents increase the bulk of a solid pharmaceutical composition, and may make a pharmaceutical dosage form containing the composition easier for the patient and care giver to handle. Diluents for solid compositions include, but are not limited to, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, or talc.

Solid pharmaceutical compositions that are compacted into a dosage form, such as a tablet, may include, but are not limited to, excipients whose functions include, but are not limited to, helping to bind the active ingredient and other excipients together after compression, such as binders. Binders for solid pharmaceutical compositions include, but are not limited to, acacia, alginic acid, carbomer (e.g., CARBOPOL®), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, or starch.

The dissolution rate of a compacted solid pharmaceutical composition in the patient's stomach may be increased by the addition of a disintegrant to the composition. Excipients which function as disintegrants include, but are not limited to, alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), or starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc, or tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Excipients that function as lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, or zinc stearate.

Flavoring agents and flavor enhancers make the dosage form more palatable to the patient. Common flavoring agents and flavor enhancers for pharmaceutical products that may be included in the composition of the invention include, but are not limited to, maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present disclosure, the active ingredient and any other solid excipients are suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the invention include, but are not limited to, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the present disclosure may also contain a viscosity enhancing agent to improve the mouth-feel of the product and/or coat the lining of the gastrointestinal tract. Such agents include, but are not limited to, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, or xanthan gum.

Sweetening agents such as sorbitol, saccharin, sodium saccharin, sucrose, aspartame, fructose, mannitol, or invert sugar may be added to improve the taste.

Preservatives and chelating agents such as alcohol, sodium benzoate, butylated hydroxy toluene, butylated hydroxyanisole, or ethylenediamine tetraacetic acid may be added at levels safe for ingestion to improve storage stability.

According to the invention, a liquid composition may also contain a buffer such as gluconic acid, lactic acid, citric acid or acetic acid, sodium gluconate, sodium lactate, sodium citrate, or sodium acetate.

The term "administering" or "administered" also refers, without limitation, to oral, parenteral, sublingual, buccal, transnasal, transdermal, rectal, intramuscular, intravenous, intraarterial (intracoronary), intraventricular, intrathecal, and subcutaneous routes, in any combination. In accordance with good clinical practice, the instant compounds can be administered at a dose that will produce effective beneficial effects without causing undue harmful or untoward side effects, i.e., the benefits associated with administration outweigh the detrimental effects.

By "parenteral" is meant intravenous, subcutaneous or intramuscular administration. In the methods of the present invention, the nondihydropiridine calcium channel blocker and/or amiodarone may be administered alone, simultaneously with one or more other compounds, or the compounds may be administered sequentially, in either order. It will be appreciated that the actual method and order of administration will vary according to, inter alia, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein.

In prophylactic applications, pharmaceutical compositions or medicaments are administered to a subject susceptible to, or otherwise at risk of, suffering cardiac-surgery-associated atrial fibrillation in an amount sufficient to eliminate or reduce the risk, lessen the severity, or delay the outset of the atrial fibrillation, including biochemical, histologic and/or physiologic symptoms of the injury. In therapeutic applications, compositions or medicants are administered to a subject suspected of, or already suffering from atrial fibrillation in an amount sufficient to treat, or at least partially reduce or arrest, the symptoms of the atrial fibrillation (biochemical, histologic and/or physiological). An amount adequate to accomplish therapeutic or prophylactic treatment is defined as an effective amount or a therapeutically or prophylactically effective dose. In either prophylactic or therapeutic regimens, compounds of the present invention can be administered in several doses until a desired effect has been achieved.

An effective dose or effective doses of the compositions of the present invention, for the treatment of the conditions described herein can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the compositions of this invention will be determined by the age, weight and condition or severity of disease or disorder of the subject.

Generally, dosing (e.g., an administration) can be one or more times daily, or less frequently, such as once a day, once a week, once a month, once a year, to once in a decade, etc. and may be in conjunction with other compositions as described herein.

The dosage and frequency of administration can vary depending on whether the treatment is prophylactic or therapeutic. In prophylactic applications, a relatively low dosage can be administered at relatively infrequent intervals over a long period of time. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The term "genetic marker" or "polymorphism" as used herein refers to a characteristic of a nucleotide sequence (e.g., in a chromosome) that is identifiable due to its variability among different subjects (i.e., the genetic marker or polymorphism can be a single nucleotide polymorphism, a restriction fragment length polymorphism, a microsatellite, a deletion of nucleotides, an addition of nucleotides, a substitution of nucleotides, a repeat or duplication of nucleotides, a translocation of nucleotides, and/or an aberrant or alternate splice site resulting in production of a truncated or extended form of a protein, etc., as would be well known to one of ordinary skill in the art).

A "single nucleotide polymorphism" (SNP) in a nucleotide sequence is a genetic marker that is polymorphic for two (or in some case three or four) alleles. SNPs can be present within a coding sequence of a gene, within noncoding regions of a gene and/or in an intergenic (e.g., intron) region of a gene. A SNP in a coding region in which both forms lead to the same polypeptide sequence is termed synonymous (i.e., a silent mutation) and if a different polypeptide sequence is produced, the alleles of that SNP are non-synonymous. SNPs that are not in protein coding regions can still have effects on gene splicing, transcription factor binding and/or the sequence of non-coding RNA.

The SNP nomenclature provided herein refers to the official Reference SNP (rs) identification number as assigned to each unique SNP by the National Center for Biotechnological Information (NCBI), which is available in the GenBank® database.

In some embodiments, the term genetic marker is also intended to describe a phenotypic effect of an allele or haplotype, including for example, an increased or decreased amount of a messenger RNA, an increased or decreased amount of protein, an increase or decrease in the copy number of a gene, production of a defective protein, tissue or organ, etc., as would be well known to one of ordinary skill in the art.

An "allele" as used herein refers to one of two or more alternative forms of a nucleotide sequence at a given position (locus) on a chromosome. An allele can be a nucleotide present in a nucleotide sequence that makes up the coding sequence of a gene and/or an allele can be a nucleotide in a non-coding region of a gene (e.g., in a genomic sequence). A subject's genotype for a given gene is the set of alleles the subject happens to possess. As noted herein, an individual can be heterozygous or homozygous for any allele of this invention.

Also as used herein, a "haplotype" is a set of alleles on a single chromatid that are statistically associated. It is thought that these associations, and the identification of a few alleles of a haplotype block, can unambiguously identify all other alleles in its region. The term "haplotype" is also commonly used to describe the genetic constitution of individuals with respect to one member of a pair of allelic genes; sets of single alleles or closely linked genes that tend to be inherited together.

Also as used herein, "linked" describes a region of a chromosome that is shared more frequently in family members or members of a population manifesting a particular phenotype and/or affected by a particular disease or disorder, than would be expected or observed by chance, thereby indicating that the gene or genes or other identified marker(s) within the linked chromosome region contain or are associated with an allele that is correlated with the phenotype and/or presence of a disease or disorder, or with an increased or decreased likelihood of the phenotype and/or of the disease or disorder. Once linkage is established, association studies (linkage disequilibrium) can be used to narrow the region of interest or to identify the marker (e.g., allele or haplotype) correlated with the phenotype and/or disease or disorder.

Furthermore, as used herein, the term "linkage disequilibrium" or "LD" refers to the occurrence in a population of two or more (e.g., 3, 4, 5, 6, 7, 8, 9, 10, etc.) linked alleles at a frequency higher or lower than expected on the basis of the gene frequencies of the individual genes. Thus, linkage disequilibrium describes a situation where alleles occur together more often than can be accounted for by chance, which indicates that the two or more alleles are physically close on a DNA strand.

The terms "increased risk" and "decreased risk" as used herein define the level of risk that a subject has of altered effectiveness of beta blocker therapy, as compared to a control subject that does not have the polymorphisms and alleles of this invention in the control subject's nucleic acid.

A sample of this invention can be any sample containing nucleic acid of a subject, as would be well known to one of ordinary skill in the art. Nonlimiting examples of a sample of this invention include a cell, a body fluid, a tissue, a washing, a swabbing, etc., as would be well known in the art.

As used herein, "nucleic acid" encompasses both RNA and DNA, including cDNA, genomic DNA, mRNA, synthetic (e.g., chemically synthesized) DNA and chimeras, fusions and/or hybrids of RNA and DNA. The nucleic acid can be double-stranded or single-stranded. Where single-stranded, the nucleic acid can be a sense strand or an antisense strand. In some embodiments, the nucleic acid can be synthesized using oligonucleotide analogs or derivatives (e.g., inosine or phosphorothioate nucleotides, etc.). Such oligonucleotides can be used, for example, to prepare nucleic acids that have altered base-pairing abilities or increased resistance to nucleases.

An "isolated nucleic acid" is a nucleotide sequence or nucleic acid molecule that is not immediately contiguous with nucleotide sequences or nucleic acid molecules with which it is immediately contiguous (one on the 5' end and one on the 3' end) in the naturally occurring genome of the organism from which it is derived or in which it is detected or identified. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid encoding an additional polypeptide, peptide sequence and/or other gene product.

The term "isolated" can also refer to a nucleic acid or polypeptide that is substantially free of cellular material, viral material, and/or culture medium (e.g., when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

The term "oligonucleotide" refers to a nucleic acid sequence of at least about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 30 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., as are well known in the art.

The present invention further provides fragments of the nucleic acids of this invention, which can be used, for example, as primers and/or probes. Such fragments or oligonucleotides can be detectably labeled or modified, for example, to include and/or incorporate a restriction enzyme cleavage site when employed as a primer in an amplification (e.g., PCR) assay.

The detection of a polymorphism, genetic marker or allele of this invention can be carried out according to various protocols standard in the art and as described herein for analyzing nucleic acid samples and nucleotide sequences, as well as identifying specific nucleotides in a nucleotide sequence.

For example, nucleic acid can be obtained from any suitable sample from the subject that will contain nucleic acid and the nucleic acid can then be prepared and analyzed according to well-established protocols for the presence of genetic markers according to the methods of this invention.

In some embodiments, analysis of the nucleic acid can be carried by amplification of the region of interest, according to protocols well known in the art (e.g., polymerase chain reaction, ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA), etc.). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers according to the methods of this invention.

In some embodiments of this invention, detection of an allele or combination of alleles of this invention can be carried out by an amplification reaction and single base extension. In particular embodiments, the product of the amplification reaction and single base extension is spotted on a silicone chip.

In yet additional embodiments, detection of an allele or combination of alleles of this invention can be carried out by matrix-assisted laser desorption/ionization-time of flight mass spectrometry (MALDI-TOF-MS).

It is further contemplated that the detection of an allele or combination of alleles of this invention can be carried out by various methods that are well known in the art, including, but not limited to nucleic acid sequencing, hybridization assay, restriction endonuclease digestion analysis, electrophoresis, and any combination thereof.

The genetic markers (e.g., alleles) of this invention are correlated with (i.e., identified to be statistically associated with) altered effectiveness of beta blocker therapy as described herein according to methods well known in the art and as disclosed in the Examples provided herein for statistically correlating genetic markers with various phenotypic traits, including disease states and pathological conditions as well as determining levels of risk associated with developing a particular phenotype, such as a disease or pathological condition. In general, identifying such correlation involves conducting analyses that establish a statistically significant association and/or a statistically significant correlation between the presence of a genetic marker or a combination of markers and the phenotypic trait in a population of subjects and controls (e.g., a population of subjects in whom the phenotype is not present or has not been detected). The correlation can involve one or more than one genetic marker of this invention (e.g., two, three, four, five, or more) in any combination. An analysis that identifies a statistical association (e.g., a significant association) between the marker or combination of markers and the phenotype establishes a correlation between the presence of the marker or combination of markers in a population of subjects and the particular phenotype being analyzed. A level of risk (e.g., increased or decreased) can then be determined for an individual on the basis of such population-based analyses.

In some embodiments, the methods of correlating genetic markers with disease states and effective treatments and/or therapies of this invention can be carried out using a computer database. Thus the present invention provides a computer-assisted method of identifying a proposed treatment and/or appropriate treatment for a subject carrying a genetic marker of this invention. The method involves the steps of (a) storing a database of biological data for a plurality of subjects, the biological data that is being stored including for each of said plurality of subjects, for example, (i) a treatment type, (ii) at least one genetic marker associated with altered effectiveness of beta blocker therapy and (iii) at least one disease progression measure for atrial fibrillation from which treatment efficacy can be determined; and then (b) querying the database to determine the correlation between the presence of said genetic marker and the effectiveness of a treatment type, to thereby identify a proposed treatment as an effective treatment.

In some embodiments, treatment information for a subject is entered into the database (through any suitable means such as a window or text interface), genetic marker information for that subject is entered into the database, and disease progression information is entered into the database. These steps are then repeated until the desired number of subjects has been entered into the database. The database can then be queried to determine whether a particular treatment is effective for subjects carrying a particular marker or combination of markers, not effective for subjects carrying a particular marker or combination of markers, etc. Such querying can be carried out prospectively or retrospectively on the database by any suitable means, but is generally done by statistical analysis in accordance with known techniques, as described herein.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present invention is more particularly described in the following examples that are intended as illustrative only since numerous modifications and variations therein will be apparent to those skilled in the art.

EXAMPLES

Example I

G Protein-coupled Receptor Kinase 5 Gene Polymorphisms are Associated with Postoperative Atrial Fibrillation after Coronary Artery Bypass Grafting in Patients Receiving β-Blockers The genes coding for β-adrenergic receptors and hepatic metabolism of several beta blockers (BBs) are highly polymorphic. Potentially relevant functional polymorphisms that affect pharmacodynamic and pharmacokinetic responses of BBs have been identified in adrenergic receptor and signaling/regulatory proteins and cytochrome P450 (CYP) 2D6 enzyme. These polymorphisms impact the risk for cardiovascular complications during BB therapy. Therefore, we examined genetic variations in the adrenergic signaling pathway and in BB biotransformation by CYP2D6 for association with new-onset postoperative AF in the setting of CABG surgery.

Study Design and Description of Study Populations

We conducted a case-cohort study in 960 patients of self-reported European ancestry who participated in the Perioperative Genetics and Safety Outcomes Study (PEGASUS), a longitudinal study approved by the Institutional Review Board at Duke University Medical Center, and who underwent isolated CABG surgery with cardiopulmonary bypass (CPB) between 1997 and 2006.[12] For patients who had more than one cardiac surgery during that period, only data from the first surgery were included. Case subjects in this study were patients receiving perioperative BB therapy who developed new-onset postoperative AF after CABG surgery. Control subjects were patients receiving perioperative BB therapy who did not develop new-onset postoperative AF. Perioperative BB therapy was defined as acute or chronic preoperative BB treatment (regardless of the type of BB) and postoperative BB treatment administered before new onset of postoperative AF. Patients with a history of preoperative AF, and patients who received no perioperative BB treatment before new-onset postoperative AF were identified by individual chart and 12-lead electrocardiogram reviews, and excluded. Of the original 960 patients, 563 met our criteria for case or control subjects and comprised the discovery cohort for our study.

CATHeterization GENetics (CATHGEN) is another longitudinal study approved by the Institutional Review Board at Duke University Medical Center.[13] We selected patients in the CATHGEN biorepository who underwent cardiac catheterization between 2001 and 2010 for evaluation of ischemic heart disease. From this group, 475 individuals of self-reported European ancestry subsequently underwent CABG surgery with CPB between 2006 and 2010, and also had available genotype data. Of these, 245 patients met our study eligibility criteria and comprised the replication cohort for our study.

Intraoperative anesthetic, perfusion, and cardioprotective management was standardized. General anesthesia was maintained with a combination of fentanyl and isoflurane. Perfusion support consisted of nonpulsatile CPB (30° C.-32° C.), crystalloid prime, pump flow rates >2.4 L/min per m$^2$, cold blood cardioplegia, α-stat blood gas management, activated clotting times >450 seconds maintained with heparin, ε-aminocaproic acid infusion administered routinely, and serial hematocrits maintained at >0.18.

Data Collection and End-point Definition

Patient demographics, preoperative and procedural factors, and perioperative medication use, which are components of the postoperative AF Risk Index (Table 3) were recorded and collated, using the Duke Information System for Cardiovascular Care—an integral part of the Duke Databank for Cardiovascular Disease. The postoperative AF Risk Index is a predictor of postoperative AF for patients undergoing cardiac surgery. Diagnosis of new-onset postoperative AF was based on postoperative electrocardiogram or rhythm strip or documented by at least 2 of the following: progress notes, nursing notes, discharge summary, or change in medication.

Candidate Gene and Marker Selection

Genomic DNA was isolated from whole blood using standard procedures. Genotyping in the PEGASUS cohort (discovery samples) was performed on the Illumina Human610-Quad BeadChip and in the CATHGEN (replication samples) cohort on Illumina OMNI1-Quad BeadChip at the Duke Genomic Analysis Facility. The Illumina raw data were analyzed using the Illumina GenomeStudio and a low GenCall score cutoff of 0.15. Each intensity plot was then examined with manual curation of genotype calls. Since single nucleotide polymorphism (SNP) arrays used in both cohorts were different, not all markers identified in the discovery cohort were present on Illumina OMNI1-Quad BeadChip used in the CATHGEN cohort. Therefore, we included imputed SNPs derived from IMPUTE2 using 1000 genome as the reference panel in CATHGEN cohort to match selected candidate SNPs between the two datasets. We excluded markers with MAF <0.05 derived from all samples of PEGASUS. Hardy-Weinberg Equilibrium (HWE) was computed for the PEGASUS and CATHGEN controls, respectively, using PLINK 1.07 software. Markers that deviated from HWE, based on Bonferroni correction (0.05/number of markers) were also excluded.

Based on the current understanding of the pharmacogenetic effects of adrenergic receptor signaling and biotransformation of BBs, a set of 10 candidate genes with a potential for modulating the effectiveness of BB therapy (Table 4) was selected, representing adrenergic receptor subtypes, intracellular secondary messenger signaling, and hepatic metabolism of BBs by the polymorphic enzyme cytochrome P450 2D6 (CYP2D6). We selected SNPs within these candidate genes and 50 kbp flanking regions outside of the gene boundary that met the quality control criteria in the discovery dataset as described above. However, there were no SNPs available in CYP2D6 due to low genotyping quality. We proceeded with imputation for CYP2D6 in the discovery dataset using IMPUTE2 and 1000 genome as the reference panel. For this imputation, we required that the probability of the best-imputed genotype be greater than 90%. A list of genotyped candidate gene polymorphisms studied is provided in Table 5.

Statistical Analysis

Descriptive statistics of clinical variables are presented as frequency and percentage for categorical variables and mean±SD or median (interquartile range) for continuous variables. Univariable logistic regression analysis was performed to test the differences in demographic and clinical and procedural characteristics between case and control subjects. P-values (P) were derived from 2-sided Wald tests. Analyses of clinical variables were conducted using SAS Version 9.2 (SAS Institute Inc., Cary, N.C.).

All association analyses below were performed using PLINK (pngu.mgh.harvard.edu/~purcell/plink/) For each of the SNPs, allelic associations with postoperative AF were assessed using logistic regression analyses adjusted for the postoperative AF Risk Index. These association tests, including those for imputed genotypes, were performed assuming an additive inheritance model (homozygote major allele vs. heterozygote vs. homozygote minor allele). To account for multiple comparisons in the discovery cohort, a false discovery rate was computed for all identified SNPs using the q-value and computed using the QVALUE program (genomics.princeton.edu/storeylab/qvalue/). The top candidate SNPs were chosen based on a q-value <20% for replication in the CATHGEN cohort. The same logistic regression model adjusted for the postoperative AF Risk Index was applied in the replication dataset.

To assess the overall effect of candidate SNPs, we then conducted a meta-analysis using the weighted Z-score meta-analysis as implemented in METAL (sph.umich.edu/csg/abecasis/metal). For the final candidate gene(s) prioritized by meta-analysis P-values, we also performed finemapping to increase the coverage using all imputed markers within the gene or region in the discovery dataset. Given that genetic effect size is often small, one common concern in a genetic association study is the impact of the winner's curse—a phenomenon of overestimated effect size for the significant markers in the discovery dataset due to ascertainment bias, that may lead to underpowered follow-up studies and failure to replicate the original findings.[23] Therefore, we evaluated the potential effect of winner's curse by applying the ascertainment-corrected maximum likelihood estimators (MLE) to assess effect sizes of the final significant markers (csg.sph.umich.edu/boehnke/winner/).

In addition, we also performed 2-marker haplotype association tests by sliding windows with the step size of one marker to scan through all markers within each gene in the discovery cohort using the standard Expectation-Maximization (E-M) algorithm implemented in PLINK to infer haplotypes. Haplotype association tests were also based on logistic regression models with adjustment for the postoperative AF Risk Index. Pairs of markers with the highest level of association were then tested in the replication dataset.

Demographics and clinical characteristics of the patients in the discovery and replication cohorts stratified according to the actual documented presence or absence of postoperative AF are shown in Table 1. The mean age of the discovery cohort was 62.5±10.5 years; 422 (75%) of the subjects were male; and the median (IQR) postoperative AF risk score was 11 (5-17). Of the 563 patients in this cohort, 111 (19.7%) developed postoperative AF. These case subjects had a significantly higher median postoperative AF risk score compared to controls without postoperative AF (13 [7-23] vs. 11 [5-17]; OR=1.06; 95% CI: 1.04-1.09; P<0.0001). A total of 561 SNPs (524 genotyped and 37 imputed) were initially available. None of the 561 candidate SNPs deviated from HWE (P<8.9×10$^{-5}$, based on Bonferroni-corrected threshold of 561 markers), but 51 genotyped and 18 imputed SNPs were excluded due to MAF <0.05. Therefore, 492 SNPs were analyzed in the discovery dataset as shown in Table 5. A total of 4 SNPs, all within the GRK5 gene, met our prespecified significance threshold of q-value ≤0.20 (P ranges from 4.78×10$^{-5}$ to 0.0015) in the discovery cohort and were selected for follow-up analysis in the replication dataset (Table 2). The genotype frequencies for these 4 SNPs in both cohorts are summarized in Table 6. The risk allele "A" of rs3740563 was the most statistically significant SNP associated with an increased risk for postoperative AF despite perioperative BB prophylaxis (odds ratio [OR]=2.75; 95% confidence interval [CI]=1.69, 4.48; P=4.78*10$^{-5}$). The other 3 SNPs also showed increased risk for postoperative AF despite perioperative BB therapy (Table 2).

As for the well-known candidate gene, CYP2D6, 19 imputed SNPs with MAF ≥0.05 were analyzed (Table 5). Five SNPs reached nominal significance (P-values ranging from 0.032 to 0.046), which included rs16947, a missense variant (OR=1.41; 95% CI: 1.00-1.97; P=0.047). However, none of these markers remained statistically significant after adjusting for multiple testing.

In the replication cohort (n=245), postoperative AF was observed in 42 (17.1%) patients. The mean age of this cohort was 61.0±10.7 years; 156 (63.7%) of the patients were male; and the median (IQR) postoperative AF risk score was 6 (1-12). Similar to the discovery cohort, patients with postoperative AF had a significantly higher mean postoperative AF risk score compared to patients without postoperative AF (11.5 [6-18] vs. 6 [0-12]; OR=1.09; 95% CI: 1.04-1.13; P=0.0001). Of the 4 SNPs analyzed in the replication cohort, 3 SNPs (rs10787959, rs3740563, and rs11198893), all in the intragenic region of GRK5, remained significantly associated with postoperative AF despite perioperative BB use (based on the Bonferroni corrected threshold of four SNP tested, P-values ranging from 0.007 to 0.016, Table 2). The meta-analysis of both datasets by METAL showed rs3740563 as the most significant SNP associated with postoperative AF despite perioperative BB prophylaxis (meta P=1.66×10$^{-6}$) with the same direction of effect in both discovery and replication datasets (Table 2). Finally, to assess the impact of ascertainment bias (winner's curse) on our findings, we compared the ORs of our most significant marker (rs3740563) derived from MLE without and with ascertainment correction. The difference between un-corrected MLE (naive MLE) and corrected was minimal in the discovery (uncorrected OR, 2.19 versus ascertainment-corrected OR, 2.28) and replication (uncorrected OR, 2.34 versus ascertainment-corrected OR, 2.37) datasets.

We further finemapped GRK5 in the discovery cohort using all qualified imputed markers (MAF ≥0.05; 389 markers) within the gene. The average distance between markers is 588.17 base-pairs (SD=675.54 bp). The rs3740563 remained the most significant marker. The linkage disequilibrium (LD) among the markers in GRK5 shows that the most significant SNP, rs3740563, is in strong LD with the adjacent SNP, rs4752292 ($r^2$=0.69). Two-marker haplotype association tests across the GRK5 region revealed an interesting region: rs11198878-rs3740563-rs4752292. In this region, despite perioperative BB therapy, association with increased risk for postoperative AF was most significant in the haplotype A-A of rs3740563-rs4752292 (OR=2.75; 95% CI: 1.69-4.48; P=0.000048). In the discovery cohort, the frequency of this haplotype (A-A) was estimated to be 7.7% in controls and 15.8% in cases. In the replication cohort, the estimated frequency was 8.5% in controls and 17.9% in cases, and remained nominally significant with an increased risk for postoperative AF (OR=2.60; 95% CI: 2.35-2.85; P=0.011).

This study is the first to demonstrate that genetic variation in the GRK5 gene is associated with postoperative AF in patients who undergo CABG surgery and were treated with perioperative BBs. These findings suggest an independent association even after adjusting for clinical and procedural variables known to predict an increased risk for postoperative AF. Thus, testing for these genetic markers could improve risk stratification and potentially personalize therapy for preventing postoperative AF.

In conclusion, in patients treated with perioperative BB, variants in GRK5 are independently associated with postoperative AF following CABG surgery. The functional significance of these polymorphisms may provide new insights into the pathogenesis of postoperative AF and modulation of response to BB therapy. This may inform the development of a perioperative strategy to personalize treatment options for new-onset postoperative AF.

Variations and modifications of the herein described systems, apparatuses, methods and other applications will undoubtedly suggest themselves to those skilled in the art. Accordingly, the foregoing description should be taken as illustrative and not in a limiting sense.

Any patents, publications, sequences and other references mentioned in this specification are indicative of the levels of those skilled in the art to which the invention pertains. These patents, publications, sequences and references are incorporated by reference herein to the same extent as if each was specifically and individually indicated to be incorporated by reference herein.

SEQUENCES OF THE INVENTION
GRK5 SNPs
rs3740563

(SEQ ID NO: 1)
GCTTACTTTCTCTAGTTTGCAGTTT[A/C]

TTTGTGTATAAACTGGAGACACTAA

-continued

Illumina 650K array: A/C change
5' near 30 bp (SEQ ID NO: 2)
AAGTAGCTTACTTTCTCTAGTTTGCAGTTT 3' near 30 bp (SEQ ID NO: 3)
TTTGTGTATAAACTGGAGACACTAACACCA FASTA sequence
>gnl|dbSNP|rs3740563|allelePos = 501|
totalLen = 1001|taxid = 9606|snpclass =
1|alleles = 'A/C'|mol = Genomic|build =
142

(SEQ ID NO: 4)
GAGTCTCACT CTGTCCCCCA GGCTGGAGTG CAGTGGTGTA

ATCTTGGCTC ATTGCAACCT

CTGCCTCCCA GATTCAAGCA ATTCTTCTGC CTCAGTCTCC

CAAGTAGCTG GGACTACAGG

TACCTGCCAC CACGCCTAGC TAATTTTGTG TTTTTAGTAG

AGACAGGGTT TCACCATGTT

GGCCAGGCTG GTCTCGAACT CCTGACCTCA TGTGATCCAC

CTGCCTTGGC CTCCCCAAGT

GCTGGGATTA CAGGCGTGAG CCACTGCGCC CAGCCTGCGC

ATGTTCTTTA AACCAGACAC

TGGCTAACAG ATACTTGTTA AGCTCCTCCT CTGTGCTAGG

CATTGCTGCA GTCACCGGAC

TTGTGTCACA GGCCACCCTT GTCCAGCAGC GAGGGCTCCT

GGAAGGATCT CTGTCACTGT

CATCAAGATG AAGTGGTGGT GCTGCTGCTG CCAGCCCTGT

GACTTTGAGC AAGTAGCTTA

CTTTCTCTAG TTTGCAGTTT

M

TTTGTGTATA AACTGGAGAC ACTAACACCA ACCTGGTAGA

GCCTCTGGGA AGGCCAGCAG

AGTGTTGCAC ACAGGCCATC ATTGTCATCA GCATCGTCAT

TGTCATCGTC ATCCTCACGG

CGATAGTGGT TTGAGGGCAG AGGTTGAGGA CCCTTTGAGA

GGGTTTTGGA GTTTCCCAGA

GAAGCTGAAT CGGCTACACA TGATGGATGA GGCCAGCTGT

TTTTGTGCTG AGGTGAAGTG

GGTTCAGTGT CCCAGAGACT GTTGCCTTGG AGTCATCGGA

ATCCTCCTCT TCCTAGAGCA

CTGCCTCCAG CTTCCTCTTC TTGGAAGCCT GCCCTGATTC

CTGCAGTCCT CAGCCTTCCT

TCCTCCCCAC GGCTCCACAG TTTGCCCAGG GAAGCTGGAA

GCATCACACT CTGCCCAGGC

CCCTGCTCTG GCCCAGTGTG TTTCCTTGAA AGGACGTGTG

TCATCTAGAA GCCTGCAGCC

CCGAGTCCTA ACAATGGTTA rs4752292

(SEQ ID NO: 5)
GACTATCATCTTCCTTGCCCAGACA[G/T]
CAGATATCATTTAAAATGGAAACCT

Illumina 650K array: G/T change
5' near 30 bp (SEQ ID NO: 6)
GCCTCGACTATCATCTTCCTTGCCCAGACA 3' near 30 bp (SEQ ID NO: 7)
CAGATATCATTTAAAATGGAAACCTGTGGG FASTA sequence
>gnl|dbSNP|rs4752292|allelePos = 501|
totalLen = 1001|taxid = 9606|snpclass =
1|alleles = 'G/T'|mol = Genomic|build =
142

(SEQ ID NO: 8)
TTTTTGAGAC AGAGTCTCAC TCCGTCACCC ATTCTGGAGT

GCAGTGATGC AGTCTCACTC

ACTGCAACCC CCGCCTCCTG GGTTCAAATG ATTCTCATGC

CTCAGCCTCC CAAGTAGCTG

GGATTACAGG TGTGCGCCAC CACGCCCAGC TAAATTTTGT

ATTTTTAATA GAGACAGGGC

TTTGCCATAT TGGCCAGGCT GGTCTTGAAC TCTTGGCCTC

AAGTAATCTG CCCACCTCAG

CCTCCCAAAG TGGCTGGGAT TACAGGTGTC AGCCACCATG

CCCAGCCCCA AAACTTACTT

TTAATTCCTT TTCTCATTAC AAAAATAATA TATGTCAATG

GTTGCAATTT CCAAAACAAT

TTTAAAAGGG GAAAATAAAA ACTGCCAATG AGATAAGGAT

AAACACTGTT AACACTTTGG

TCTGTTGCCC TTTTGTAGTT TGTTCTGCTT CTAGGGAGAG

AATTGTACCA GCCTCGACTA

TCATCTTCCT TGCCCAGACA

K

CAGATATCAT TTAAAATGGA AACCTGTGGG TTGTAGAATC

CCCCTTGGAC TGGGAGGCAG

AAGACCCAGT TTCTTGTGTT ACCACTTGGT CCTGTGGCCT

TGGGAAAGCC ACTTAACCTT

GATTTGCTCG TCTTTAAAAT GGGGACTCAG TATTCCTCAC

CTTAGCAGAT GGAGTGGCCA

AAGGTGTTTC TGGCAGAGAG TGCTTTGCAA AGTGCTGTGC

AAATTGCTGG CCAGTTTTGA

TGTGGGTGTG TGAGCCTTTG GTTGGACAAA TGGCCAGAGT

AGTTTTCCTG TCTTCTTGGG

GGAACTGTGA CCCTTTCTCG TAAAGCTGTT CTGTCTCTGA

TCCTGGTGAA CATCACCAGC

TTCCTCTAGC TGCCCAGAGC TGCCCCTCCC CTCTGCCCTG

CCGTGTGGCA CCTGGCCCAG

TGCAGTGTCC AGTCCCTCTC CAGGTCCCGA TGCCTCGGCC

TCCACAGTAT CTCCTAGTCT

GCCCCTCTCG CCCCATCTCC rs11198893
(SEQ ID NO: 9)
AAGATGCTGTGGATCGTTTTGGGAA[A/G]

TAAGCAGGCAATGAATAAGTCAGTG

Illumina 650K array, A/G change
5' near 30 bp
(SEQ ID NO: 10)
ATTGGAAGATGCTGTGGATCGTTTTGGGAA 3' near 30 bp
(SEQ ID NO: 11)
TAAGCAGGCAATGAATAAGTCAGTGCGTTA FASTA sequence
>gnl|dbSNP|rs11198893|allelePos = 201|
totalLen = 401|taxid = 9606|snpclass =
1|alleles = 'A/G'|mol = Genomic|build =
142
(SEQ ID NO: 12)
GCATCCCTCT TTCTTCAAAC TGCTGGGAAG CCCATAGCTC

AGTTTGATGT CAAAAGCAAA

GCTCTCTTTC ATCTGATGTC ATCGGGGAG CTCATTTGAT

TTTCCCCTCC CTCTTTTGCT

GTTTGTTTCC TGTTCTTTGT CTTTTATGGA ACAATTGAAC

ATGTGCCTTT ATTGGAAGAT

GCTGTGGATC GTTTTGGGAA

R

TAAGCAGGCA ATGAATAAGT CAGTGCGTTA GAAACGAAGG

GGAGAAGAAG CTCCCTGCTC

GGCCTAGGAA GCAGGCAGGT CTGAGCCTTG TTCCTCCTCT

CTGGAGAATG GACATATGGG

CACCTGCCCT GTAGACCTTG AGGAATGAGA ACAGAATGGG

TTCTGGTGGT CCAGTGTGCT

GGGCAGCAAT GGGCATGTCC rs10787959
(SEQ ID NO: 13)
AAGATGCTGTGGATCGTTTTGGGAA[A/G]

TAAGCAGGCAATGAATAAGTCAGTG

Illumina 650K array, A/G change
5' near 30 bp
(SEQ ID NO: 14)
ACCCATCATTTCCTGAGTCTGATAGAGGAG 3' near 30 bp
(SEQ ID NO: 15)
TAGGATCTGTCCAGTGGCTGCTGTTTCTGT FASTA sequence
>gnl|dbSNP|rs10787959|allelePos = 501|
totalLen = 1001|taxid = 9606|snpclass =
1|alleles = 'A/G'|mol = Genomic|build =
142
(SEQ ID NO: 16)
GGAAGCTGGG CCGCCCTCAC TGCCTGTGTC CTCGCCACCT

CCTATTGGGA AACTCTGGTT

GCCCTCCAAG AGTCCACATA CTGCAGGCTC TTAATTAAGA

AAGTATGTTC CCATTTCATG

TCACTCGAAA AGAATGAAAA CAGTGACAGC ATTTATTTAT

CTTAACTATC AATATCATTC

CTGTTTCTCA GTCCGCTGGG GGTATGAGTC TTGAAGGAAT

TGACTGGGTT ATGAGATTTG

AACCTCGGGC ATGTGCTGGT GGGACACATG TGGCCTGCTT

CCGAGAAGGA GCCTTGAAGG

AAGAGCAAGC AGGCTGGCAT GGCCCTGCCC TGCCCTGCCC

TCCCGGAGCT CAGGGCCGAA

GGGCTCGGTG ACAGTGGGGA ACTCCTGCCT GCTTTGGTGC

TAATGGAGAG TCAAGGTTCC

TTTTTCACCA GCTACCTCCT ATCTCCTTTC TCAGTCATCG

GAGAAGTAAA ACCCATCATT

TCCTGAGTCT GATAGAGGAG

R

TAGGATCTGT CCAGTGGCTG CTGTTTCTGT GGCACCTACT

GTGTGCTGAG GCTGGGCCAG

GTGCTCACAT GCGTTGTTGC CAATCCCCGG CAGCAACCAG

CTAACTCTGA TGGCCTCAGG

TAAAGGGACT TGCCCAAGAC CACACAGCCA TCCAGAGTTG

CTCCACTGTG GAGACACTAT

TGCCATTTGG AGCAGAATAA TTATGTGTGG CAGGGAGCTG

TCCTGTGCAT TGTGGGGTAT

TTAGCACATC CCTGGCCTCC ACCCACTAAT CAGTAGTAAC

CTCACAGTTG TGATAACACA

AAATGTCTAC AGACATTGCC AAAATTTCCC GCTGCTGAAA

ACCTCTGAGC TAGGGGATGG

AGGTAGGATT CAGACCCAAG CCTGTGCTTG TTCGCCACCC

TGTGCTAGCT CTGAAGAAGT

CCTCACCCAA GCAAGGCAAC CCTGCTTGCC TTTAGGATCC

AGGCAGCGTG GTAGTGCTTT

GGTGTTTCTG AACTATGTAC

TABLE 1

Demographic, Clinical and Procedural Characteristics of the Study Populations based on Postoperative Atrial Fibrillation Risk Index

| | DISCOVERY DATASET (N = 563) | | | | REPLICATION DATASET (N = 245) | | | |
|---|---|---|---|---|---|---|---|---|
| Predictor | No PoAF (n = 452) | Yes PoAF (n = 111) | OR (95% CI) | P-value* | No PoAF (n = 203) | Yes PoAF (n = 42) | OR (95% CI) | P-value* |
| Age, y | 61.3 ± 10.2 | 67.4 ± 10.3 | 1.06 (1.04-1.08) | <0.0001 | 59.1 ± 10.6 | 64.8 ± 10.0 | 1.05 (1.02-1.09) | <0.0001 |
| Medical History | | | | | | | | |
| Atrial Fibrillation | 0 | 0 | | | 0 | 0 | | |
| Chronic obstructive pulmonary disease | 31 (5.5) | 9 (1.6) | 1.20 (0.56-2.60) | 0.64 | 12 (4.9) | 3 (1.2) | 1.22 (0.33-4.54) | 0.76 |
| Concurrent valve surgery | 0 | 0 | | | 0 | 0 | | |
| Withdrawal of Postoperative Treatment | 0 | 0 | | | 0 | 0 | | |
| Beta-blocker | 188 (33.4) | 52 (9.2) | 1.24 (0.82-1.89) | 0.32 | 96 (38.4) | 20 (8.2) | 1.05 (0.54-2.05) | 0.88 |
| ACE inhibitor | | | | | | | | |
| Beta-blocker Treatment | 452 (100) | 111 (100) | 1.0 | | 179 (73.1) | 33 (13.5) | 0.49 (0.21-1.15) | 0.1 |
| Preoperative and Postoperative | 452 (100) | 111 (100) | 1.0 | | 24 (9.8) | 9 (3.7) | 2.03 (0.87-2.80) | 0.1 |
| Postoperative | 60 (10.7) | 15 (2.7) | 1.02 (0.56-1.89) | 0.94 | 42 (17.1) | 4 (1.6) | 0.40 (0.14-1.19) | 0.1 |
| Preoperative and Postoperative ACE Inhibitor Treatment | 156 (27.7) | 41 (7.3) | 1.11 (0.72-1.71) | 0.63 | 107 (43.7) | 17 (6.9) | 0.61 (0.31-1.20) | 0.15 |
| Preoperative and Postoperative Statin Treatment | | | | | | | | |
| Postoperative Treatment | | | | | | | | |
| Potassium Supplementation | 394 (69.9) | 81 (14.4) | 0.40 (0.24-0.66) | 0.0003 | 179 (70.1) | 31 (12.7) | 0.38 (0.17-0.85) | 0.02 |
| NSAIDs | 98 (17.4) | 14 (2.5) | 0.52 (0.29-0.95) | 0.03 | 57 (23.2) | 4 (2.0) | 0.27 (0.09-0.79) | 0.017 |
| Postoperative AF risk index | 11 [5-17] | 13 [7-23] | 1.06 (1.04-1.09) | <0.0001 | 6 [0-12] | 11.5 [6-18] | 1.09 (1.04-1.13) | 0.0001 |

Continuous variables are presented as means ± standard deviation, or median [interquartile range], and categorical variables as percent frequencies. OR (95% CI), univariate odds ratio (95% confidence interval)
*Comparisons were made using logistic regression to test the differences in demographic, clinical and procedural characteristics between cases and controls, where p-values were derived from the Wald tests. Patients in the discovery and replication sets are separated by actual documented presence or absence of postoperative AF.

TABLE 2

Logistic Regression Analysis of Genetic Predictors of Postoperative Atrial Fibrillation in the Study Populations

| | | | DISCOVERY DATASET (N = 563) | | | | REPLICATION DATASET (N = 245) | | | | | |
|---|---|---|---|---|---|---|---|---|---|---|---|---|
| | | | MAF | | | | MAF | | | | | |
| Model variables | Base pair | Gene location | No PoAF | Yes PoAF | OR (95% CI) | P-value | No PoAF | Yes PoAF | OR (95% CI) | P-value | Meta-analysis P-value | Direction[†] |
| GRK5[‡] | | | | | | | | | | | | |
| rs3740563 | 121095400 | Intron | 0.09 | 0.16 | 2.75 (1.69-4.48) | 4.78*10$^{-5}$ | 0.10 | 0.18 | 2.60 (1.24-5.45) | 0.011 | 1.66*10$^{-6}$ | ++ |
| rs4752292 | 121100153 | Intron | 0.13 | 0.20 | 2.21 (1.44-3.39) | 0.00027 | 0.15 | 0.21 | 1.74 (0.93-3.27) | 0.085 | 6.88*10$^{-5}$ | ++ |
| rs11198893 | 121107900 | Intron | 0.08 | 0.13 | 2.51 (1.49-4.24) | 0.00054 | 0.08 | 0.15 | 2.58 (1.20-5.57) | 0.016 | 2.43*10$^{-5}$ | ++ |
| rs10787959 | 121131313 | Intron | 0.26 | 0.33 | 1.72 (1.23-2.40) | 0.0015 | 0.27 | 0.39 | 2.07 (1.23-3.50) | 0.007 | 3.39*10$^{-5}$ | ++ |

MAF, minor allele frequency in cases and controls;
OR, multivariate odds ratio;
PoAF, postoperative atrial fibrillation;
SNP, single nucleotide polymorphism
*P-values are expressed using the Wald test
[†]Summary of effect direction for each study, with one "+" per study
[‡]Adjusted for postoperative atrial fibrillation risk index as a continuous variable.

TABLE 3

Predictors of the postoperative Atrial Fibrillation Risk Index after coronary artery bypass surgery*

| Predictor | Risk score |
|---|---|
| Age, y | |
| <30 | 0 |
| 30-39 | 6 |
| 40-49 | 12 |
| 50-59 | 18 |
| 60-69 | 24 |
| 70-79 | 30 |
| ≥80 | 36 |

TABLE 3-continued

Predictors of the postoperative Atrial Fibrillation
Risk Index after coronary artery bypass surgery*

| Predictor | Risk score |
|---|---|
| Medical history | |
| Atrial fibrillation | 7 |
| Chronic obstructive pulmonary disease | 4 |
| Concurrent valve surgery | 5 |
| Withdrawal of postoperative treatment | |
| β-blockers | 7 |
| Angiotensin converting enzyme inhibitors | 7 |
| Preoperative and postoperative treatment | |
| β-blockers | −7 |
| Angiotensin converting enzyme inhibitors | −5 |
| Statins | −5 |
| Postoperative β-blockers | −11 |
| Other postoperative treatment | |
| Potassium supplementation | −5 |
| Non-steroidal anti-inflammatory drugs | −7 |

*A risk score <7 is associated with 11.7% chance of developing postoperative atrial fibrillation (low risk); 7-24 with 30.3% (medium risk); and >24 with 66.9% chance (high risk). (1, 2)

TABLE 4

Adrenergic Receptors or Related Genes with Potential Implications
for Pharmacogenomics of Adrenergic Receptor Signaling

| Receptor/Protein | Chromosome | Gene | Relevant cardiovascular function |
|---|---|---|---|
| Pharmacodynamics | | | |
| $\alpha_{2A}$ | 10q25.2 | ADRA2A | Its stimulation results in prevention of norepinephrine release from sympathetic nerve endings in the heart, decreased sympathetic tone and blood pressure |
| $\alpha_{2C}$ | 4p16 | ADRA2C | Its stimulation by epinephrine or norepinephrine results in decreased norepinephrine release from the presynaptic nerve terminals |
| $\beta_1$ | 10q25.3 | ADRB1 | Positive inotropic, chronotropic and lusitropic effects in the heart |
| $\beta_2$ | 5q31-q32 | ADRB2 | Vascular smooth muscle cell relaxation, whereas in cardiac myocytes increased inotropic, chronotropic, and antiapoptotic effects |
| GRK2 | 11q13.1 | ADRBK1 | Determines the rate and extent of β-adrenergic receptor desensitization and resensitization |
| GRK5 | 10q26.11 | GRK5 | Determines the rate and extent of β-adrenergic receptor desensitization and resensitization |
| G α s | 20q13.3 | GNAS | Stimulates adenyl cyclase to produce cAMP, which by activating protein kinase A exerts cellular effects of β-adrenergic receptor activation |
| $\beta_1$-arrestin | 11q13 | ARRB1 | A cytosolic protein and acts as a cofactor in the beta-adrenergic receptor kinase mediated desensitization of $\beta_1$-adrenergic receptor |
| $\beta_2$-arrestin | 17p13 | ARRB2 | Like $\beta_1$-arrestin, it inhibits β-adrenergic receptor function |
| Pharmacokinetics | | | |
| Cytochrome P450 2D6 | 22q13.1 | CYP2D6 | Involved in the hepatic elimination of lipophilic β-blockers (metoprolol, propranolol, carvedilol, labetalol and timolol) |

ADRA2A and ADRA2C: http://www.ncbi.nlm.nih.gov/gene/150
ADRB1 and ADRB2: (1)
GRK2: http://www.ncbi.nlm.nih.gov/gene/156
GRK5: http://www.ncbi.nlm.nih.gov/gene/2869
GNAS: (2)
ARRB1: http://www.ncbi.nlm.nih.gov/gene?cmd=Retrieve&dopt=full report&list uids=408
ARRB2: http://www.ncbi.nlm.nih.gov/gene/409
CYP2D6: http://www.ncbi.nlm.nih.gov/gene/1565
References:
(1). Kertai M D, Fontes M, Podgoreanu M V. Pharmacogenomics of beta-blockers and statins: possible implications for perioperative cardiac complications. J Cardiothorac Vasc Anesth 2012; 26: 1101-14.
(2). Lymperopoulos A, Rengo G, Koch W J. GRK2 inhibition in heart failure: something old, something new. Curr Pharm Des 2012; 18: 186-91.

TABLE 5

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 4 | RS2857962 | 3737883 | LOC100129786 \| ADRA2C | INTERGENIC | G | 0.08363 | 1 | 0.5824 | 1.717 | 0.9999 |
| 4 | RS4916611 | 3652592 | LOC100129786 \| ADRA2C | INTERGENIC | A | 0.08526 | 1.325 | 0.7662 | 2.291 | 0.3139 |
| 4 | RS13118771 | 3765755 | LOC100129786 \| ADRA2C | INTERGENIC | G | 0.08703 | 0.7301 | 0.4056 | 1.314 | 0.2942 |
| 4 | RS4916612 | 3750155 | LOC100129786 \| ADRA2C | INTERGENIC | A | 0.09236 | 1.107 | 0.6724 | 1.822 | 0.6897 |
| 4 | RS2880892 | 3683269 | LOC100129786 \| ADRA2C | INTERGENIC | A | 0.09503 | 0.8268 | 0.4787 | 1.428 | 0.495 |
| 4 | RS177773 | 3661211 | LOC100129786 \| ADRA2C | INTERGENIC | A | 0.09928 | 1.181 | 0.7265 | 1.919 | 0.5028 |
| 4 | RS7692883 | 3762123 | LOC100129786 \| ADRA2C | INTERGENIC | A | 0.09947 | 0.7723 | 0.4556 | 1.309 | 0.3372 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 4 | RS4916617 | 3670686 | LOC100129786 | ADRA2C | INTERGENIC | A | 0.1101 | 1.215 | 0.7458 | 1.98 | 0.4338 |
| 4 | RS16844747 | 3668328 | LOC100129786 | ADRA2C | INTERGENIC | A | 0.1281 | 1.13 | 0.7207 | 1.77 | 0.5951 |
| 4 | RS17203086 | 3661134 | LOC100129786 | ADRA2C | INTERGENIC | A | 0.1909 | 0.9537 | 0.6439 | 1.412 | 0.8129 |
| 4 | RS1894441 | 3734895 | LOC100129786 | ADRA2C | INTERGENIC | G | 0.1945 | 1.005 | 0.6837 | 1.477 | 0.9806 |
| 4 | RS2748789 | 3710982 | LOC100129786 | ADRA2C | INTERGENIC | A | 0.2016 | 0.8792 | 0.5904 | 1.309 | 0.5265 |
| 4 | RS2748787 | 3714659 | LOC100129786 | ADRA2C | INTERGENIC | C | 0.2167 | 0.9134 | 0.6224 | 1.34 | 0.6436 |
| 4 | RS4916622 | 3687360 | LOC100129786 | ADRA2C | INTERGENIC | G | 0.2327 | 1.289 | 0.9026 | 1.841 | 0.1625 |
| 4 | RS177766 | 3669171 | LOC100129786 | ADRA2C | INTERGENIC | G | 0.2726 | 1.439 | 1.035 | 2.001 | 0.03055 |
| 4 | RS11731847 | 3659574 | LOC100129786 | ADRA2C | INTERGENIC | A | 0.3171 | 0.9716 | 0.7043 | 1.34 | 0.8609 |
| 4 | RS16844797 | 3713599 | LOC100129786 | ADRA2C | INTERGENIC | A | 0.3455 | 0.9949 | 0.7319 | 1.352 | 0.974 |
| 4 | RS177776 | 3658742 | LOC100129786 | ADRA2C | INTERGENIC | G | 0.3694 | 1.004 | 0.7377 | 1.367 | 0.9779 |
| 4 | RS177778 | 3657065 | LOC100129786 | ADRA2C | INTERGENIC | G | 0.3759 | 0.9372 | 0.6874 | 1.278 | 0.6817 |
| 4 | RS177769 | 3664206 | LOC100129786 | ADRA2C | INTERGENIC | A | 0.379 | 1.01 | 0.7403 | 1.378 | 0.95 |
| 4 | RS11938629 | 3719380 | LOC100129786 | ADRA2C | INTERGENIC | G | 0.3828 | 0.9336 | 0.6887 | 1.265 | 0.6577 |
| 4 | RS4498196 | 3747842 | LOC100129786 | ADRA2C | INTERGENIC | C | 0.389 | 0.8798 | 0.6487 | 1.193 | 0.4105 |
| 4 | RS2748777 | 3719829 | LOC100129786 | ADRA2C | INTERGENIC | A | 0.3929 | 1.098 | 0.8067 | 1.495 | 0.5524 |
| 4 | RS7375509 | 3721299 | LOC100129786 | ADRA2C | INTERGENIC | A | 0.3952 | 1.116 | 0.8221 | 1.515 | 0.4818 |
| 4 | RS2857960 | 3740612 | LOC100129786 | ADRA2C | INTERGENIC | C | 0.4059 | 0.9048 | 0.6614 | 1.238 | 0.5313 |
| 4 | RS885797 | 3703725 | LOC100129786 | ADRA2C | INTERGENIC | A | 0.4174 | 1.124 | 0.8261 | 1.529 | 0.457 |
| 4 | RS2857969 | 3712082 | LOC100129786 | ADRA2C | INTERGENIC | A | 0.4254 | 1.04 | 0.7648 | 1.413 | 0.8038 |
| 4 | RS177798 | 3644957 | LOC100129786 | ADRA2C | INTERGENIC | A | 0.4343 | 1.088 | 0.8014 | 1.477 | 0.5889 |
| 4 | RS177795 | 3647113 | LOC100129786 | ADRA2C | INTERGENIC | A | 0.4352 | 1.085 | 0.7993 | 1.474 | 0.6002 |
| 4 | RS7377501 | 3721269 | LOC100129786 | ADRA2C | INTERGENIC | C | 0.4449 | 1.061 | 0.788 | 1.428 | 0.6968 |
| 4 | RS4916632 | 3706785 | LOC100129786 | ADRA2C | INTERGENIC | C | 0.4609 | 1.121 | 0.8235 | 1.525 | 0.4684 |
| 4 | RS445275 | 3742998 | LOC100129786 | ADRA2C | INTERGENIC | C | 0.4713 | 1.072 | 0.7958 | 1.443 | 0.6483 |
| 4 | RS28612860 | 3813929 | ADRA2C | LOC348926 | INTERGENIC | A | 0.1181 | 1.356 | 0.8813 | 2.087 | 0.1659 |
| 4 | RS12506413 | 3788647 | ADRA2C | LOC348926 | INTERGENIC | A | 0.1829 | 0.6321 | 0.4151 | 0.9623 | 0.03244 |
| 4 | RS28687658 | 3845104 | ADRA2C | LOC348926 | INTERGENIC | C | 0.3837 | 1.074 | 0.7918 | 1.457 | 0.6462 |
| 4 | RS3889790 | 3923728 | ADRA2C | LOC348926 | INTERGENIC | G | 0.3986 | 0.8881 | 0.653 | 1.208 | 0.4494 |
| 4 | RS4076725 | 3792209 | ADRA2C | LOC348926 | INTERGENIC | A | 0.4039 | 0.8162 | 0.5971 | 1.116 | 0.2029 |
| 4 | RS7440077 | 3792442 | ADRA2C | LOC348926 | INTERGENIC | G | 0.4245 | 0.851 | 0.6233 | 1.162 | 0.3098 |
| 4 | RS28622001 | 3793990 | ADRA2C | LOC348926 | INTERGENIC | G | 0.4272 | 0.8636 | 0.6335 | 1.177 | 0.3534 |
| 4 | RS28605619 | 3804286 | ADRA2C | LOC348926 | INTERGENIC | G | 0.4369 | 1.055 | 0.7747 | 1.436 | 0.7356 |
| 4 | RS28590539 | 3824221 | ADRA2C | LOC348926 | INTERGENIC | A | 0.444 | 0.8282 | 0.6111 | 1.122 | 0.2242 |
| 4 | RS28366830 | 3856471 | ADRA2C | LOC348926 | INTERGENIC | G | 0.4884 | 1.193 | 0.8799 | 1.617 | 0.256 |
| 4 | RS6822427 | 3780072 | ADRA2C | LOC348926 | INTERGENIC | A | 0.4902 | 1.185 | 0.8743 | 1.606 | 0.2741 |
| 4 | RS28650078 | 3866157 | ADRA2C | LOC348926 | INTERGENIC | NA | NA | NA | NA | NA | NA |
| 4 | RS28716006 | 3935145 | ADRA2C | LOC348926 | INTERGENIC | A | NA | NA | NA | NA | NA |
| 4 | RS16844858 | 3754366 | LOC100129786 | ADRA2C | INTERGENIC | G | 0.0008881 | 3.81E−09 | 0 | Infinite | 0.9994 |
| 4 | RS28528880 | 3875234 | ADRA2C | LOC348926 | INTERGENIC | A | 0.002664 | 3.821 | 0.3218 | 45.37 | 0.2883 |
| 4 | RS4916608 | 3702481 | LOC100129786 | INTERGENIC | G | 0.008007 | 1.278 | 0.2504 | 6.519 | 0.7682 |
| 5 | RS1042713 | 148206440 | ADRB2 | CODING | A | 0.3375 | 0.8422 | 0.6076 | 1.167 | 0.3026 |
| 5 | RS1042718 | 148206917 | ADRB2 | CODING | A | 0.1838 | 1.31 | 0.9111 | 1.884 | 0.1449 |
| 5 | RS1042714 | 148206473 | ADRB2 | CODING | C | 0.4377 | 1.029 | 0.768 | 1.38 | 0.8464 |
| 5 | RS1042717 | 148206646 | ADRB2 | CODING | A | 0.2167 | 1.171 | 0.8279 | 1.655 | 0.3728 |
| 5 | RS30319 | 148161051 | HTR4 | ADRB2 | INTERGENIC | G | 0.05595 | 1.26 | 0.6702 | 2.368 | 0.4733 |
| 5 | RS17640437 | 148169675 | HTR4 | ADRB2 | INTERGENIC | G | 0.06572 | 1.871 | 1.097 | 3.19 | 0.0214 |
| 5 | RS17777882 | 148118029 | HTR4 | ADRB2 | INTERGENIC | A | 0.08703 | 0.7178 | 0.4009 | 1.285 | 0.2645 |
| 5 | RS9285673 | 148172928 | HTR4 | ADRB2 | INTERGENIC | C | 0.1012 | 1.007 | 0.614 | 1.65 | 0.979 |
| 5 | RS9325113 | 148098003 | HTR4 | ADRB2 | INTERGENIC | A | 0.167 | 0.755 | 0.493 | 1.156 | 0.1961 |
| 5 | RS17640419 | 148169346 | HTR4 | ADRB2 | INTERGENIC | A | 0.1753 | 0.9551 | 0.6417 | 1.422 | 0.8209 |
| 5 | RS877741 | 148196737 | HTR4 | ADRB2 | INTERGENIC | G | 0.1909 | 0.7624 | 0.5103 | 1.139 | 0.1854 |
| 5 | RS2400642 | 148114806 | HTR4 | ADRB2 | INTERGENIC | G | 0.2211 | 0.9284 | 0.6409 | 1.345 | 0.6945 |
| 5 | RS888961 | 148038897 | HTR4 | ADRB2 | INTERGENIC | A | 0.242 | 1.01 | 0.7098 | 1.438 | 0.9542 |
| 5 | RS888956 | 148120217 | HTR4 | ADRB2 | INTERGENIC | C | 0.2478 | 0.897 | 0.6322 | 1.273 | 0.5425 |
| 5 | RS6580582 | 148173382 | HTR4 | ADRB2 | INTERGENIC | G | 0.286 | 0.8566 | 0.6139 | 1.195 | 0.3626 |
| 5 | RS12654778 | 148205741 | HTR4 | ADRB2 | INTERGENIC | A | 0.3366 | 0.8598 | 0.6225 | 1.187 | 0.359 |
| 5 | RS13177640 | 148074640 | HTR4 | ADRB2 | INTERGENIC | A | 0.389 | 0.8432 | 0.6181 | 1.15 | 0.2816 |
| 5 | RS3923307 | 148073605 | HTR4 | ADRB2 | INTERGENIC | G | 0.3908 | 0.8385 | 0.6153 | 1.143 | 0.2644 |
| 5 | RS1820076 | 148045282 | HTR4 | ADRB2 | INTERGENIC | A | 0.4075 | 0.9373 | 0.6891 | 1.275 | 0.6801 |
| 5 | RS10476898 | 148056656 | HTR4 | ADRB2 | INTERGENIC | G | 0.4094 | 0.9296 | 0.6841 | 1.263 | 0.6407 |
| 5 | RS6580567 | 148102208 | HTR4 | ADRB2 | INTERGENIC | A | 0.4279 | 0.8591 | 0.6386 | 1.156 | 0.3158 |
| 5 | RS2082382 | 148200553 | HTR4 | ADRB2 | INTERGENIC | G | 0.4352 | 1.02 | 0.7601 | 1.369 | 0.8944 |
| 5 | RS1820074 | 148054452 | HTR4 | ADRB2 | INTERGENIC | G | 0.4378 | 0.9285 | 0.6889 | 1.252 | 0.6264 |
| 5 | RS2400707 | 148205052 | HTR4 | ADRB2 | INTERGENIC | A | 0.4385 | 1.031 | 0.7705 | 1.38 | 0.836 |
| 5 | RS11168068 | 148204121 | HTR4 | ADRB2 | INTERGENIC | G | 0.4414 | 1.042 | 0.7781 | 1.395 | 0.7833 |
| 5 | RS6580565 | 148098702 | HTR4 | ADRB2 | INTERGENIC | G | 0.4485 | 0.8355 | 0.6226 | 1.121 | 0.2311 |
| 5 | RS4425495 | 148060817 | HTR4 | ADRB2 | INTERGENIC | G | 0.4574 | 0.91 | 0.677 | 1.223 | 0.5319 |
| 5 | RS30328 | 148166447 | HTR4 | ADRB2 | INTERGENIC | A | 0.4716 | 1.012 | 0.7474 | 1.37 | 0.9391 |
| 5 | RS30325 | 148163324 | HTR4 | ADRB2 | INTERGENIC | G | 0.4725 | 1.014 | 0.7483 | 1.374 | 0.9293 |
| 5 | RS30330 | 148168332 | HTR4 | ADRB2 | INTERGENIC | A | 0.4725 | 1.009 | 0.7452 | 1.367 | 0.9529 |
| 5 | RS2163752 | 148145138 | HTR4 | ADRB2 | INTERGENIC | G | 0.4787 | 1.102 | 0.8172 | 1.486 | 0.5244 |
| 5 | RS30306 | 148152364 | HTR4 | ADRB2 | INTERGENIC | A | 0.4787 | 1.101 | 0.8168 | 1.485 | 0.5271 |
| 5 | RS30312 | 148156653 | HTR4 | ADRB2 | INTERGENIC | A | 0.4796 | 1.091 | 0.8082 | 1.474 | 0.5683 |
| 5 | RS171551 | 148172689 | HTR4 | ADRB2 | INTERGENIC | A | 0.5 | 1.159 | 0.8564 | 1.569 | 0.3386 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 5 | RS2053044 | 148205372 | ADRB1 | C10orf118 | INTERGENIC | A | 0.4387 | 1.031 | 0.7698 | 1.38 | 0.839 |
| 5 | RS1029942 | 148310151 | ADRB2 | SH3TC2 | INTERGENIC | G | 0.05773 | 1.291 | 0.6816 | 2.447 | 0.4327 |
| 5 | RS17653341 | 148332864 | ADRB2 | SH3TC2 | INTERGENIC | A | 0.06927 | 1.062 | 0.5907 | 1.909 | 0.841 |
| 5 | RS6580586 | 148242723 | ADRB2 | SH3TC2 | INTERGENIC | C | 0.1048 | 0.8126 | 0.4818 | 1.371 | 0.4366 |
| 5 | RS1181141 | 148280187 | ADRB2 | SH3TC2 | INTERGENIC | C | 0.1146 | 0.8315 | 0.5022 | 1.377 | 0.4732 |
| 5 | RS6897548 | 148342056 | ADRB2 | SH3TC2 | INTERGENIC | G | 0.1226 | 1.153 | 0.7452 | 1.784 | 0.5225 |
| 5 | RS2895822 | 148340823 | ADRB2 | SH3TC2 | INTERGENIC | G | 0.1228 | 1.151 | 0.7442 | 1.782 | 0.5267 |
| 5 | RS17640705 | 148251784 | ADRB2 | SH3TC2 | INTERGENIC | A | 0.1323 | 0.9866 | 0.6171 | 1.577 | 0.9551 |
| 5 | RS4705284 | 148287096 | ADRB2 | SH3TC2 | INTERGENIC | A | 0.1368 | 0.9952 | 0.6282 | 1.576 | 0.9836 |
| 5 | RS11957970 | 148297564 | ADRB2 | SH3TC2 | INTERGENIC | A | 0.1554 | 1.133 | 0.7476 | 1.717 | 0.5563 |
| 5 | RS1181135 | 148285597 | ADRB2 | SH3TC2 | INTERGENIC | G | 0.1622 | 0.8801 | 0.5757 | 1.345 | 0.5553 |
| 5 | RS7725267 | 148339859 | ADRB2 | SH3TC2 | INTERGENIC | A | 0.1681 | 0.9012 | 0.5943 | 1.367 | 0.6243 |
| 5 | RS17640574 | 148217864 | ADRB2 | SH3TC2 | INTERGENIC | A | 0.1767 | 0.9331 | 0.6137 | 1.419 | 0.7458 |
| 5 | RS3857420 | 148213082 | ADRB2 | SH3TC2 | INTERGENIC | A | 0.1821 | 1.095 | 0.7455 | 1.608 | 0.6439 |
| 5 | RS10515621 | 148246544 | ADRB2 | SH3TC2 | INTERGENIC | G | 0.1829 | 0.7338 | 0.4867 | 1.106 | 0.1396 |
| 5 | RS7737361 | 148346443 | ADRB2 | SH3TC2 | INTERGENIC | A | 0.1865 | 1.144 | 0.7874 | 1.663 | 0.4796 |
| 5 | RS10045726 | 148352990 | ADRB2 | SH3TC2 | INTERGENIC | G | 0.1927 | 0.6476 | 0.4289 | 0.9779 | 0.03882 |
| 5 | RS994446 | 148348395 | ADRB2 | SH3TC2 | INTERGENIC | A | 0.2096 | 1.321 | 0.9349 | 1.866 | 0.1146 |
| 5 | RS4705292 | 148305032 | ADRB2 | SH3TC2 | INTERGENIC | A | 0.2131 | 1.146 | 0.7937 | 1.653 | 0.4681 |
| 5 | RS4705286 | 148302641 | ADRB2 | SH3TC2 | INTERGENIC | G | 0.2149 | 1.175 | 0.8151 | 1.694 | 0.3871 |
| 5 | RS13189358 | 148240456 | ADRB2 | SH3TC2 | INTERGENIC | A | 0.2398 | 1.516 | 1.063 | 2.163 | 0.02165 |
| 5 | RS11959113 | 148228496 | ADRB2 | SH3TC2 | INTERGENIC | A | 0.2411 | 0.9989 | 0.7002 | 1.425 | 0.9952 |
| 5 | RS6888011 | 148221473 | ADRB2 | SH3TC2 | INTERGENIC | G | 0.3295 | 1.269 | 0.9152 | 1.759 | 0.1531 |
| 5 | RS6888329 | 148216402 | ADRB2 | SH3TC2 | INTERGENIC | G | 0.3313 | 0.8998 | 0.6535 | 1.239 | 0.5173 |
| 5 | RS11168074 | 148291305 | ADRB2 | SH3TC2 | INTERGENIC | G | 0.333 | 1.221 | 0.8793 | 1.694 | 0.2336 |
| 5 | RS973057 | 148329991 | ADRB2 | SH3TC2 | INTERGENIC | A | 0.3348 | 0.998 | 0.7247 | 1.374 | 0.9905 |
| 5 | RS919725 | 148261996 | ADRB2 | SH3TC2 | INTERGENIC | A | 0.3401 | 1.352 | 0.9724 | 1.88 | 0.07285 |
| 5 | RS10491338 | 148309644 | ADRB2 | SH3TC2 | INTERGENIC | C | 0.3544 | 0.9733 | 0.7019 | 1.35 | 0.8711 |
| 5 | RS741146 | 148307111 | ADRB2 | SH3TC2 | INTERGENIC | A | 0.3544 | 0.9733 | 0.7019 | 1.35 | 0.8711 |
| 5 | RS7720732 | 148343086 | ADRB2 | SH3TC2 | INTERGENIC | A | 0.3583 | 0.9667 | 0.7057 | 1.324 | 0.8331 |
| 5 | RS10875641 | 148292922 | ADRB2 | SH3TC2 | INTERGENIC | G | 0.3659 | 0.8623 | 0.6195 | 1.2 | 0.3801 |
| 5 | RS4705285 | 148287177 | ADRB2 | SH3TC2 | INTERGENIC | A | 0.3677 | 0.8317 | 0.5978 | 1.157 | 0.2737 |
| 5 | RS11740830 | 148281930 | ADRB2 | SH3TC2 | INTERGENIC | C | 0.3719 | 1.187 | 0.8536 | 1.65 | 0.3087 |
| 5 | RS759135 | 148331571 | ADRB2 | SH3TC2 | INTERGENIC | C | 0.3845 | 0.7922 | 0.5701 | 1.101 | 0.1652 |
| 5 | RS17707884 | 148236409 | ADRB2 | SH3TC2 | INTERGENIC | A | 0.3881 | 0.8297 | 0.6023 | 1.143 | 0.2532 |
| 5 | RS4705064 | 148313933 | ADRB2 | SH3TC2 | INTERGENIC | G | 0.3908 | 0.9587 | 0.6963 | 1.32 | 0.7961 |
| 5 | RS7729953 | 148312767 | ADRB2 | SH3TC2 | INTERGENIC | G | 0.4005 | 0.917 | 0.6685 | 1.258 | 0.5914 |
| 5 | RS2116756 | 148356738 | ADRB2 | SH3TC2 | INTERGENIC | C | 0.4057 | 0.9367 | 0.6888 | 1.274 | 0.6766 |
| 5 | RS733032 | 148357632 | ADRB2 | SH3TC2 | INTERGENIC | A | 0.4059 | 0.9381 | 0.6911 | 1.273 | 0.6818 |
| 5 | RS10075995 | 148293429 | ADRB2 | SH3TC2 | INTERGENIC | G | 0.4192 | 0.9344 | 0.6849 | 1.275 | 0.6687 |
| 5 | RS9325124 | 148248818 | ADRB2 | SH3TC2 | INTERGENIC | A | 0.4245 | 1.245 | 0.9049 | 1.713 | 0.1782 |
| 5 | RS11742519 | 148238308 | ADRB2 | SH3TC2 | INTERGENIC | C | 0.4423 | 1.338 | 0.9773 | 1.831 | 0.06928 |
| 5 | RS12652493 | 148311053 | ADRB2 | SH3TC2 | INTERGENIC | A | 0.4485 | 0.908 | 0.6614 | 1.246 | 0.5503 |
| 5 | RS4705280 | 148278925 | ADRB2 | SH3TC2 | INTERGENIC | A | 0.4663 | 1.153 | 0.8445 | 1.574 | 0.3706 |
| 5 | RS1468722 | 148295679 | ADRB2 | SH3TC2 | INTERGENIC | A | 0.4725 | 1.043 | 0.7708 | 1.411 | 0.7859 |
| 5 | RS11957757 | 148216187 | ADRB2 | SH3TC2 | INTERGENIC | A | 0.4734 | 1.125 | 0.8414 | 1.504 | 0.4268 |
| 5 | RS1864932 | 148267406 | ADRB2 | SH3TC2 | INTERGENIC | G | 0.4822 | 1.353 | 0.9817 | 1.864 | 0.06474 |
| 5 | RS1181139 | 148280902 | ADRB2 | SH3TC2 | INTERGENIC | G | 0.4867 | 1.087 | 0.7973 | 1.483 | 0.5967 |
| 5 | RS11740851 | 148306745 | ADRB2 | SH3TC2 | INTERGENIC | A | 0.4929 | 0.9615 | 0.7045 | 1.312 | 0.8046 |
| 5 | RS2400711 | 148321436 | ADRB2 | SH3TC2 | INTERGENIC | G | 0.4991 | 1.167 | 0.8586 | 1.586 | 0.3242 |
| 5 | RS17108803 | 148205556 | HTR4 | ADRB2 | INTERGENIC | NA | NA | NA | NA | NA | NA |
| 5 | RS28763957 | 148207662 | ADRB2 | UTR | G | NA | NA | NA | NA | NA |
| 5 | RS6879202 | 148207667 | ADRB2 | UTR | NA | NA | NA | NA | NA | NA |
| 5 | RS10075525 | 148130138 | HTR4 | ADRB2 | INTERGENIC | G | 0.0008881 | 4.87E−09 | 0 | Infinite | 0.9994 |
| 5 | RS33968470 | 148209011 | ADRB2 | SH3TC2 | INTERGENIC | A | 0.0008881 | 2.47E−09 | 0 | Infinite | 0.9994 |
| 5 | RS34623097 | 148204609 | HTR4 | ADRB2 | INTERGENIC | A | 0.0008881 | 1.71E−09 | 0 | Infinite | 0.9993 |
| 5 | RS10059242 | 148182123 | HTR4 | ADRB2 | INTERGENIC | G | 0.005329 | 2.867 | 0.4812 | 17.08 | 0.2474 |
| 5 | RS917875 | 148316076 | ADRB2 | SH3TC2 | INTERGENIC | C | 0.0427 | 0.9023 | 0.404 | 2.015 | 0.802 |
| 5 | RS17108911 | 148283322 | ADRB2 | SH3TC2 | INTERGENIC | G | 0.04359 | 0.9408 | 0.4472 | 1.979 | 0.8723 |
| 5 | RS10063588 | 148169107 | HTR4 | ADRB2 | INTERGENIC | A | 0.04537 | 0.4928 | 0.19 | 1.278 | 0.1455 |
| 10 | RS17128356 | 112832225 | SHOC2 | ADRA2A | INTERGENIC | A | 0.0524 | 0.8106 | 0.3985 | 1.649 | 0.5621 |
| 10 | RS10732804 | 112795021 | SHOC2 | ADRA2A | INTERGENIC | A | 0.05417 | 0.815 | 0.3984 | 1.667 | 0.5752 |
| 10 | RS7096359 | 112833561 | SHOC2 | ADRA2A | INTERGENIC | G | 0.1155 | 1.07 | 0.6682 | 1.713 | 0.7782 |
| 10 | RS491589 | 112834632 | SHOC2 | ADRA2A | INTERGENIC | A | 0.1705 | 0.9699 | 0.6468 | 1.455 | 0.8826 |
| 10 | RS10787298 | 112788041 | SHOC2 | ADRA2A | INTERGENIC | A | 0.2034 | 1.405 | 0.9694 | 2.037 | 0.0725 |
| 10 | RS1410054 | 112774155 | SHOC2 | ADRA2A | INTERGENIC | A | 0.2567 | 1.246 | 0.8749 | 1.774 | 0.2229 |
| 10 | RS521674 | 112835590 | SHOC2 | ADRA2A | INTERGENIC | T | 0.3034 | 1.15 | 0.8347 | 1.584 | 0.3928 |
| 10 | RS12776874 | 115833936 | ADRB1 | C10orf119 | INTERGENIC | A | 0.1 | 1.043 | 0.6327 | 1.718 | 0.8702 |
| 10 | RS3813719 | 115806882 | ADRB1 | C10orf120 | INTERGENIC | A | 0.1462 | 1.183 | 0.7758 | 1.803 | 0.4357 |
| 10 | RS2782977 | 115875204 | ADRB1 | C10orf121 | INTERGENIC | A | 0.1812 | 1.133 | 0.7701 | 1.666 | 0.5272 |
| 10 | RS4359161 | 115826508 | ADRB1 | C10orf122 | INTERGENIC | A | 0.1966 | 1.156 | 0.7811 | 1.71 | 0.469 |
| 10 | RS1034258 | 115832408 | ADRB1 | C10orf123 | INTERGENIC | G | 0.2558 | 0.9846 | 0.6968 | 1.391 | 0.9297 |
| 10 | RS7086063 | 115844045 | ADRB1 | C10orf124 | INTERGENIC | C | 0.2584 | 1.096 | 0.7842 | 1.533 | 0.5906 |
| 10 | RS3813720 | 115807016 | ADRB1 | C10orf125 | INTERGENIC | G | 0.3579 | 0.847 | 0.6203 | 1.156 | 0.296 |
| 10 | RS7905846 | 115850176 | ADRB1 | C10orf126 | INTERGENIC | A | 0.3854 | 1.135 | 0.8312 | 1.55 | 0.4253 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 10 | RS17776203 | 115848372 | ADRB1 | C10orf127 | INTERGENIC | C | 0.4607 | 1.097 | 0.8096 | 1.486 | 0.5513 |
| 10 | RS10885531 | 115814392 | ADRB1 | C10orf128 | INTERGENIC | A | 0.4947 | 1.058 | 0.7851 | 1.427 | 0.7094 |
| 10 | RS4918688 | 113517931 | ADRA2A | GPAM | INTERGENIC | A | 0.05249 | 1.658 | 0.9181 | 2.996 | 0.09359 |
| 10 | RS4304698 | 113512966 | ADRA2A | GPAM | INTERGENIC | G | 0.05329 | 1.903 | 1.048 | 3.455 | 0.0344 |
| 10 | RS11195714 | 113517330 | ADRA2A | GPAM | INTERGENIC | G | 0.05773 | 1.638 | 0.9216 | 2.911 | 0.09261 |
| 10 | RS3107343 | 113279085 | ADRA2A | GPAM | INTERGENIC | A | 0.05861 | 0.955 | 0.4945 | 1.845 | 0.891 |
| 10 | RS17128407 | 112865677 | ADRA2A | GPAM | INTERGENIC | A | 0.06039 | 0.8959 | 0.4632 | 1.733 | 0.7439 |
| 10 | RS3107354 | 113248711 | ADRA2A | GPAM | INTERGENIC | A | 0.06039 | 0.9406 | 0.4879 | 1.814 | 0.8549 |
| 10 | RS4587666 | 113045163 | ADRA2A | GPAM | INTERGENIC | G | 0.06306 | 0.7288 | 0.3727 | 1.425 | 0.3553 |
| 10 | RS17128709 | 113061132 | ADRA2A | GPAM | INTERGENIC | A | 0.06584 | 0.7473 | 0.3845 | 1.452 | 0.3902 |
| 10 | RS1338007 | 113522934 | ADRA2A | GPAM | INTERGENIC | A | 0.07016 | 1.554 | 0.8971 | 2.694 | 0.1158 |
| 10 | RS12778878 | 112991416 | ADRA2A | GPAM | INTERGENIC | G | 0.07105 | 0.7997 | 0.422 | 1.516 | 0.4933 |
| 10 | RS7921705 | 113284609 | ADRA2A | GPAM | INTERGENIC | A | 0.07105 | 1.273 | 0.7405 | 2.189 | 0.3825 |
| 10 | RS2792752 | 113879794 | ADRA2A | GPAM | INTERGENIC | A | 0.07282 | 1.324 | 0.7553 | 2.319 | 0.3273 |
| 10 | RS17189737 | 112979004 | ADRA2A | GPAM | INTERGENIC | A | 0.07295 | 0.9542 | 0.5328 | 1.709 | 0.8747 |
| 10 | RS2804585 | 113783588 | ADRA2A | GPAM | INTERGENIC | A | 0.07371 | 1.116 | 0.6332 | 1.967 | 0.7044 |
| 10 | RS7092820 | 113767459 | ADRA2A | GPAM | INTERGENIC | A | 0.0746 | 1.085 | 0.6163 | 1.912 | 0.7765 |
| 10 | RS7917775 | 113632807 | ADRA2A | GPAM | INTERGENIC | C | 0.0746 | 1.107 | 0.6269 | 1.956 | 0.7254 |
| 10 | RS12221264 | 112978950 | ADRA2A | GPAM | INTERGENIC | A | 0.07726 | 0.7079 | 0.3929 | 1.276 | 0.2503 |
| 10 | RS2792717 | 113787146 | ADRA2A | GPAM | INTERGENIC | G | 0.07815 | 1.307 | 0.7622 | 2.241 | 0.3306 |
| 10 | RS3125478 | 113227145 | ADRA2A | GPAM | INTERGENIC | C | 0.07829 | 0.8742 | 0.4873 | 1.568 | 0.652 |
| 10 | RS11195735 | 113582237 | ADRA2A | GPAM | INTERGENIC | A | 0.07904 | 1.172 | 0.6722 | 2.043 | 0.5763 |
| 10 | RS9543855 | 112903806 | ADRA2A | GPAM | INTERGENIC | G | 0.08082 | 1.048 | 0.6038 | 1.819 | 0.8673 |
| 10 | RS6585082 | 113261732 | ADRA2A | GPAM | INTERGENIC | A | 0.08348 | 0.9458 | 0.5405 | 1.655 | 0.8453 |
| 10 | RS12569902 | 113536366 | ADRA2A | GPAM | INTERGENIC | A | 0.08703 | 1.006 | 0.5941 | 1.703 | 0.9825 |
| 10 | RS6585125 | 113667034 | ADRA2A | GPAM | INTERGENIC | G | 0.08703 | 1.007 | 0.5948 | 1.703 | 0.9807 |
| 10 | RS10787327 | 113060979 | ADRA2A | GPAM | INTERGENIC | A | 0.08792 | 0.7596 | 0.4293 | 1.344 | 0.345 |
| 10 | RS7917681 | 113050405 | ADRA2A | GPAM | INTERGENIC | A | 0.08881 | 0.9398 | 0.5448 | 1.621 | 0.8234 |
| 10 | RS10787318 | 113040493 | ADRA2A | GPAM | INTERGENIC | A | 0.09059 | 1.066 | 0.6442 | 1.764 | 0.8039 |
| 10 | RS4918639 | 113079536 | ADRA2A | GPAM | INTERGENIC | A | 0.09147 | 0.8008 | 0.4607 | 1.392 | 0.4312 |
| 10 | RS17790693 | 113284330 | ADRA2A | GPAM | INTERGENIC | G | 0.09253 | 0.9722 | 0.5721 | 1.652 | 0.917 |
| 10 | RS17128431 | 112884869 | ADRA2A | GPAM | INTERGENIC | G | 0.09591 | 0.9114 | 0.5374 | 1.545 | 0.7305 |
| 10 | RS11817468 | 112987597 | ADRA2A | GPAM | INTERGENIC | G | 0.09947 | 1.025 | 0.6212 | 1.692 | 0.9224 |
| 10 | RS17128645 | 113015309 | ADRA2A | GPAM | INTERGENIC | A | 0.09947 | 1.025 | 0.6212 | 1.692 | 0.9224 |
| 10 | RS1335715 | 112982077 | ADRA2A | GPAM | INTERGENIC | A | 0.1004 | 1.007 | 0.6104 | 1.663 | 0.9768 |
| 10 | RS7079973 | 112937459 | ADRA2A | GPAM | INTERGENIC | C | 0.1004 | 0.997 | 0.6108 | 1.627 | 0.9903 |
| 10 | RS12354545 | 113751347 | ADRA2A | GPAM | INTERGENIC | G | 0.1012 | 1.058 | 0.6549 | 1.71 | 0.8171 |
| 10 | RS7087417 | 113744358 | ADRA2A | GPAM | INTERGENIC | A | 0.1012 | 1.047 | 0.6477 | 1.692 | 0.8517 |
| 10 | RS10749107 | 113766676 | ADRA2A | GPAM | INTERGENIC | A | 0.1021 | 0.9314 | 0.5601 | 1.549 | 0.7843 |
| 10 | RS3107373 | 113315640 | ADRA2A | GPAM | INTERGENIC | A | 0.103 | 0.8117 | 0.4882 | 1.35 | 0.4213 |
| 10 | RS7923493 | 113737605 | ADRA2A | GPAM | INTERGENIC | G | 0.103 | 1.028 | 0.6364 | 1.661 | 0.9097 |
| 10 | RS4258313 | 113032398 | ADRA2A | GPAM | INTERGENIC | A | 0.1048 | 1.021 | 0.6264 | 1.664 | 0.9334 |
| 10 | RS12244315 | 112986661 | ADRA2A | GPAM | INTERGENIC | A | 0.1066 | 1.046 | 0.6475 | 1.688 | 0.8554 |
| 10 | RS11195813 | 113858192 | ADRA2A | GPAM | INTERGENIC | A | 0.1083 | 0.9645 | 0.5811 | 1.601 | 0.8887 |
| 10 | RS10787315 | 113032549 | ADRA2A | GPAM | INTERGENIC | A | 0.1128 | 1.228 | 0.7761 | 1.942 | 0.3807 |
| 10 | RS6585041 | 112942838 | ADRA2A | GPAM | INTERGENIC | G | 0.1128 | 1.133 | 0.7206 | 1.783 | 0.588 |
| 10 | RS12573790 | 113115245 | ADRA2A | GPAM | INTERGENIC | A | 0.1155 | 0.7231 | 0.4335 | 1.206 | 0.2144 |
| 10 | RS7086940 | 113656367 | ADRA2A | GPAM | INTERGENIC | A | 0.1181 | 1.199 | 0.7752 | 1.855 | 0.4145 |
| 10 | RS2804591 | 113787569 | ADRA2A | GPAM | INTERGENIC | G | 0.1199 | 1.202 | 0.7664 | 1.884 | 0.4235 |
| 10 | RS12261976 | 113070996 | ADRA2A | GPAM | INTERGENIC | A | 0.1219 | 0.8484 | 0.5232 | 1.376 | 0.5051 |
| 10 | RS11195465 | 112954345 | ADRA2A | GPAM | INTERGENIC | G | 0.1234 | 1.02 | 0.6593 | 1.578 | 0.9294 |
| 10 | RS11195470 | 112958502 | ADRA2A | GPAM | INTERGENIC | A | 0.1234 | 1.02 | 0.6593 | 1.578 | 0.9294 |
| 10 | RS4465313 | 113072148 | ADRA2A | GPAM | INTERGENIC | A | 0.127 | 0.9014 | 0.5626 | 1.444 | 0.6659 |
| 10 | RS7088001 | 113295291 | ADRA2A | GPAM | INTERGENIC | G | 0.1272 | 1.071 | 0.6866 | 1.671 | 0.7618 |
| 10 | RS4917596 | 112944491 | ADRA2A | GPAM | INTERGENIC | G | 0.1288 | 1.064 | 0.6964 | 1.624 | 0.7756 |
| 10 | RS4348827 | 113100630 | ADRA2A | GPAM | INTERGENIC | A | 0.1297 | 0.8861 | 0.5558 | 1.413 | 0.6115 |
| 10 | RS2804616 | 113855270 | ADRA2A | GPAM | INTERGENIC | G | 0.1359 | 0.9592 | 0.6063 | 1.518 | 0.8587 |
| 10 | RS10885107 | 112941780 | ADRA2A | GPAM | INTERGENIC | G | 0.1394 | 1.079 | 0.7151 | 1.629 | 0.7161 |
| 10 | RS11195450 | 112931645 | ADRA2A | GPAM | INTERGENIC | G | 0.1394 | 1.079 | 0.7151 | 1.629 | 0.7161 |
| 10 | RS2792747 | 113897746 | ADRA2A | GPAM | INTERGENIC | G | 0.1456 | 0.9576 | 0.6211 | 1.476 | 0.8444 |
| 10 | RS11195604 | 113240800 | ADRA2A | GPAM | INTERGENIC | A | 0.1501 | 0.9134 | 0.5922 | 1.409 | 0.6821 |
| 10 | RS7069564 | 112897070 | ADRA2A | GPAM | INTERGENIC | A | 0.151 | 1.068 | 0.7002 | 1.628 | 0.7614 |
| 10 | RS10885123 | 113048321 | ADRA2A | GPAM | INTERGENIC | A | 0.1563 | 1.105 | 0.7272 | 1.678 | 0.6409 |
| 10 | RS1335712 | 112948994 | ADRA2A | GPAM | INTERGENIC | G | 0.1572 | 0.7836 | 0.5132 | 1.196 | 0.2587 |
| 10 | RS1421050 | 113754544 | ADRA2A | GPAM | INTERGENIC | C | 0.1581 | 0.8117 | 0.5309 | 1.241 | 0.3353 |
| 10 | RS4372376 | 113231124 | ADRA2A | GPAM | INTERGENIC | A | 0.1661 | 0.9478 | 0.6277 | 1.431 | 0.7987 |
| 10 | RS10509948 | 113489049 | ADRA2A | GPAM | INTERGENIC | A | 0.1758 | 1.022 | 0.6917 | 1.511 | 0.9119 |
| 10 | RS11195534 | 113106287 | ADRA2A | GPAM | INTERGENIC | A | 0.177 | 1.069 | 0.7234 | 1.579 | 0.7387 |
| 10 | RS12220858 | 112919665 | ADRA2A | GPAM | INTERGENIC | G | 0.1776 | 0.6647 | 0.4341 | 1.018 | 0.06033 |
| 10 | RS1556716 | 112867412 | ADRA2A | GPAM | INTERGENIC | G | 0.1812 | 0.9497 | 0.6464 | 1.395 | 0.7927 |
| 10 | RS9420082 | 113166617 | ADRA2A | GPAM | INTERGENIC | G | 0.1918 | 0.9396 | 0.6377 | 1.384 | 0.7526 |
| 10 | RS10885154 | 113151980 | ADRA2A | GPAM | INTERGENIC | A | 0.1954 | 0.8878 | 0.5985 | 1.317 | 0.5541 |
| 10 | RS6585077 | 113171138 | ADRA2A | GPAM | INTERGENIC | G | 0.1972 | 0.9442 | 0.6418 | 1.389 | 0.7708 |
| 10 | RS11195680 | 113449034 | ADRA2A | GPAM | INTERGENIC | G | 0.1989 | 0.9389 | 0.633 | 1.393 | 0.7541 |
| 10 | RS7917960 | 113155506 | ADRA2A | GPAM | INTERGENIC | A | 0.206 | 0.9577 | 0.6528 | 1.405 | 0.8251 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 10 | RS10749064 | 113040471 | ADRA2A \| GPAM | INTERGENIC | G | 0.2096 | 0.9677 | 0.6679 | 1.402 | 0.8624 |
| 10 | RS10749065 | 113040544 | ADRA2A \| GPAM | INTERGENIC | A | 0.2096 | 0.9677 | 0.6679 | 1.402 | 0.8624 |
| 10 | RS1953734 | 113489458 | ADRA2A \| GPAM | INTERGENIC | G | 0.2105 | 1.19 | 0.8294 | 1.708 | 0.3448 |
| 10 | RS10787324 | 113053676 | ADRA2A \| GPAM | INTERGENIC | A | 0.214 | 0.9581 | 0.6586 | 1.394 | 0.8229 |
| 10 | RS3885682 | 113059322 | ADRA2A \| GPAM | INTERGENIC | A | 0.2185 | 0.8703 | 0.5945 | 1.274 | 0.475 |
| 10 | RS7916268 | 113295975 | ADRA2A \| GPAM | INTERGENIC | A | 0.2185 | 0.907 | 0.622 | 1.322 | 0.6117 |
| 10 | RS7082000 | 113117827 | ADRA2A \| GPAM | INTERGENIC | G | 0.222 | 1.352 | 0.9609 | 1.903 | 0.08345 |
| 10 | RS6585037 | 112901012 | ADRA2A \| GPAM | INTERGENIC | A | 0.2256 | 1.171 | 0.8275 | 1.657 | 0.3729 |
| 10 | RS6585063 | 113077472 | ADRA2A \| GPAM | INTERGENIC | G | 0.2274 | 0.8496 | 0.5821 | 1.24 | 0.3984 |
| 10 | RS10885203 | 113279678 | ADRA2A \| GPAM | INTERGENIC | A | 0.23 | 1.126 | 0.797 | 1.591 | 0.501 |
| 10 | RS7903217 | 113104470 | ADRA2A \| GPAM | INTERGENIC | C | 0.23 | 0.7986 | 0.5516 | 1.156 | 0.2335 |
| 10 | RS2138551 | 113234700 | ADRA2A \| GPAM | INTERGENIC | A | 0.2327 | 0.9419 | 0.6606 | 1.343 | 0.7406 |
| 10 | RS11195633 | 113333303 | ADRA2A \| GPAM | INTERGENIC | G | 0.2371 | 0.897 | 0.6314 | 1.275 | 0.5443 |
| 10 | RS10885138 | 113107362 | ADRA2A \| GPAM | INTERGENIC | A | 0.2442 | 0.8869 | 0.6196 | 1.27 | 0.512 |
| 10 | RS3107340 | 113294887 | ADRA2A \| GPAM | INTERGENIC | A | 0.254 | 1.199 | 0.8601 | 1.672 | 0.284 |
| 10 | RS11195665 | 113415191 | ADRA2A \| GPAM | INTERGENIC | G | 0.2567 | 0.9602 | 0.6814 | 1.353 | 0.8167 |
| 10 | RS10787384 | 113444821 | ADRA2A \| GPAM | INTERGENIC | G | 0.262 | 1.025 | 0.7304 | 1.438 | 0.8872 |
| 10 | RS10885223 | 113396689 | ADRA2A \| GPAM | INTERGENIC | A | 0.2655 | 0.9371 | 0.6682 | 1.314 | 0.7065 |
| 10 | RS7910523 | 113504084 | ADRA2A \| GPAM | INTERGENIC | C | 0.2727 | 1.142 | 0.8209 | 1.589 | 0.4303 |
| 10 | RS745557 | 112846298 | ADRA2A \| GPAM | INTERGENIC | G | 0.2843 | 0.8233 | 0.5833 | 1.162 | 0.2687 |
| 10 | RS12240818 | 112979757 | ADRA2A \| GPAM | INTERGENIC | A | 0.2877 | 0.7177 | 0.5024 | 1.025 | 0.06838 |
| 10 | RS1889744 | 112970743 | ADRA2A \| GPAM | INTERGENIC | G | 0.2877 | 0.7209 | 0.5053 | 1.029 | 0.0711 |
| 10 | RS4620658 | 113158055 | ADRA2A \| GPAM | INTERGENIC | G | 0.2886 | 1.051 | 0.7607 | 1.453 | 0.762 |
| 10 | RS4597006 | 113011293 | ADRA2A \| GPAM | INTERGENIC | G | 0.2895 | 0.7312 | 0.5129 | 1.042 | 0.08355 |
| 10 | RS6585043 | 113010056 | ADRA2A \| GPAM | INTERGENIC | A | 0.2897 | 0.7303 | 0.5123 | 1.041 | 0.08239 |
| 10 | RS1878248 | 113321761 | ADRA2A \| GPAM | INTERGENIC | A | 0.2904 | 0.9151 | 0.6571 | 1.274 | 0.5996 |
| 10 | RS7083899 | 113613125 | ADRA2A \| GPAM | INTERGENIC | A | 0.9204 | 1.093 | 0.7818 | 1.527 | 0.604 |
| 10 | RS7476362 | 113000317 | ADRA2A \| GPAM | INTERGENIC | G | 0.2931 | 0.7462 | 0.5248 | 1.061 | 0.1032 |
| 10 | RS945332 | 112963152 | ADRA2A \| GPAM | INTERGENIC | A | 0.2936 | 0.7782 | 0.5535 | 1.094 | 0.1493 |
| 10 | RS11195662 | 113408669 | ADRA2A \| GPAM | INTERGENIC | A | 0.294 | 0.9208 | 0.6611 | 1.282 | 0.6253 |
| 10 | RS7923518 | 113619670 | ADRA2A \| GPAM | INTERGENIC | G | 0.2948 | 1.099 | 0.7891 | 1.53 | 0.5775 |
| 10 | RS1337987 | 113538188 | ADRA2A \| GPAM | INTERGENIC | A | 0.2975 | 1.015 | 0.7322 | 1.407 | 0.9288 |
| 10 | RS2203615 | 113293749 | ADRA2A \| GPAM | INTERGENIC | A | 0.2975 | 1.029 | 0.7278 | 1.456 | 0.8702 |
| 10 | RS10509951 | 113516620 | ADRA2A \| GPAM | INTERGENIC | A | 0.2993 | 1.073 | 0.7708 | 1.492 | 0.6778 |
| 10 | RS1415848 | 113504180 | ADRA2A \| GPAM | INTERGENIC | A | 0.302 | 1.276 | 0.9288 | 1.753 | 0.1325 |
| 10 | RS10885273 | 113558585 | ADRA2A \| GPAM | INTERGENIC | G | 0.3028 | 1.04 | 0.7529 | 1.437 | 0.8112 |
| 10 | RS3120592 | 113373981 | ADRA2A \| GPAM | INTERGENIC | A | 0.3087 | 0.9876 | 0.7171 | 1.36 | 0.9389 |
| 10 | RS1414882 | 113471552 | ADRA2A \| GPAM | INTERGENIC | A | 0.3114 | 0.9175 | 0.6592 | 1.277 | 0.6101 |
| 10 | RS602618 | 112843085 | ADRA2A \| GPAM | INTERGENIC | C | 0.3117 | 1.08 | 0.781 | 1.495 | 0.6402 |
| 10 | RS10885243 | 113445582 | ADRA2A \| GPAM | INTERGENIC | G | 0.3126 | 0.9263 | 0.6667 | 1.287 | 0.6482 |
| 10 | RS7084501 | 112859699 | ADRA2A \| GPAM | INTERGENIC | G | 0.3158 | 1.103 | 0.7911 | 1.539 | 0.5623 |
| 10 | RS7897445 | 112872557 | ADRA2A \| GPAM | INTERGENIC | A | 0.3215 | 1.015 | 0.7357 | 1.4 | 0.9283 |
| 10 | RS10885112 | 112960963 | ADRA2A \| GPAM | INTERGENIC | G | 0.323 | 0.9822 | 0.7171 | 1.345 | 0.9109 |
| 10 | RS10749089 | 113213538 | ADRA2A \| GPAM | INTERGENIC | A | 0.3277 | 1.141 | 0.8312 | 1.566 | 0.415 |
| 10 | RS10885189 | 113213105 | ADRA2A \| GPAM | INTERGENIC | A | 0.3277 | 1.141 | 0.8312 | 1.566 | 0.415 |
| 10 | RS12779426 | 113507338 | ADRA2A \| GPAM | INTERGENIC | G | 0.3339 | 1.258 | 0.9257 | 1.711 | 0.1423 |
| 10 | RS1362785 | 113697366 | ADRA2A \| GPAM | INTERGENIC | A | 0.3419 | 1.216 | 0.8923 | 1.656 | 0.216 |
| 10 | RS10885145 | 113140675 | ADRA2A \| GPAM | INTERGENIC | A | 0.3428 | 1.011 | 0.7404 | 1.38 | 0.9469 |
| 10 | RS3107358 | 113245619 | ADRA2A \| GPAM | INTERGENIC | C | 0.3428 | 1.089 | 0.801 | 1.482 | 0.5851 |
| 10 | RS953196 | 113290300 | ADRA2A \| GPAM | INTERGENIC | A | 0.3428 | 1.116 | 0.8185 | 1.522 | 0.4875 |
| 10 | RS945335 | 112887549 | ADRA2A \| GPAM | INTERGENIC | A | 0.3455 | 1.039 | 0.7548 | 1.429 | 0.816 |
| 10 | RS7908645 | 112856425 | ADRA2A \| GPAM | INTERGENIC | C | 0.3517 | 0.9908 | 0.7178 | 1.368 | 0.955 |
| 10 | RS11195715 | 113519624 | ADRA2A \| GPAM | INTERGENIC | A | 0.3535 | 1.196 | 0.8797 | 1.627 | 0.253 |
| 10 | RS582128 | 113652440 | ADRA2A \| GPAM | INTERGENIC | G | 0.3541 | 1.147 | 0.8436 | 1.559 | 0.3821 |
| 10 | RS7079277 | 112882742 | ADRA2A \| GPAM | INTERGENIC | G | 0.3597 | 1.014 | 0.7406 | 1.39 | 0.929 |
| 10 | RS10749099 | 113534724 | ADRA2A \| GPAM | INTERGENIC | C | 0.3615 | 1.015 | 0.7433 | 1.386 | 0.925 |
| 10 | RS7894045 | 113511441 | ADRA2A \| GPAM | INTERGENIC | A | 0.3636 | 1.193 | 0.8772 | 1.623 | 0.2605 |
| 10 | RS1415847 | 113536606 | ADRA2A \| GPAM | INTERGENIC | G | 0.3677 | 1.008 | 0.7381 | 1.376 | 0.9614 |
| 10 | RS869244 | 112909105 | ADRA2A \| GPAM | INTERGENIC | A | 0.3721 | 1.157 | 0.8416 | 1.59 | 0.3696 |
| 10 | RS7901717 | 113593918 | ADRA2A \| GPAM | INTERGENIC | A | 0.3737 | 1.129 | 0.8344 | 1.527 | 0.4319 |
| 10 | RS10509953 | 113593116 | ADRA2A \| GPAM | INTERGENIC | G | 0.3783 | 1.135 | 0.8329 | 1.546 | 0.4233 |
| 10 | RS10509944 | 113282918 | ADRA2A \| GPAM | INTERGENIC | A | 0.3792 | 0.9259 | 0.681 | 1.259 | 0.6234 |
| 10 | RS11195719 | 113538688 | ADRA2A \| GPAM | INTERGENIC | G | 0.3819 | 1.061 | 0.7844 | 1.435 | 0.7011 |
| 10 | RS1336432 | 113358246 | ADRA2A \| GPAM | INTERGENIC | A | 0.3826 | 0.9197 | 0.6782 | 1.247 | 0.5899 |
| 10 | RS1537768 | 112969627 | ADRA2A \| GPAM | INTERGENIC | C | 0.3854 | 0.759 | 0.5544 | 1.04 | 0.08578 |
| 10 | RS1878247 | 113318464 | ADRA2A \| GPAM | INTERGENIC | G | 0.3854 | 0.8791 | 0.6424 | 1.203 | 0.4208 |
| 10 | RS17775850 | 112994448 | ADRA2A \| GPAM | INTERGENIC | A | 0.3881 | 0.7692 | 0.5606 | 1.055 | 0.1039 |
| 10 | RS4508142 | 113011038 | ADRA2A \| GPAM | INTERGENIC | G | 0.389 | 0.7828 | 0.5707 | 1.074 | 0.1287 |
| 10 | RS7896901 | 113010359 | ADRA2A \| GPAM | INTERGENIC | A | 0.389 | 0.7828 | 0.5707 | 1.074 | 0.1287 |
| 10 | RS2792743 | 113903510 | ADRA2A \| GPAM | INTERGENIC | A | 0.3917 | 1.253 | 0.918 | 1.709 | 0.1555 |
| 10 | RS4468280 | 113053039 | ADRA2A \| GPAM | INTERGENIC | G | 0.3917 | 1.096 | 0.8039 | 1.493 | 0.5629 |
| 10 | RS1337988 | 113489715 | ADRA2A \| GPAM | INTERGENIC | A | 0.3925 | 0.925 | 0.6785 | 1.261 | 0.6219 |
| 10 | RS959127 | 113611569 | ADRA2A \| GPAM | INTERGENIC | G | 0.3934 | 1.187 | 0.8787 | 1.603 | 0.2641 |
| 10 | RS7098615 | 113139169 | ADRA2A \| GPAM | INTERGENIC | C | 0.397 | 0.9084 | 0.669 | 1.233 | 0.5381 |
| 10 | RS12257178 | 113016228 | ADRA2A \| GPAM | INTERGENIC | G | 0.3979 | 0.7556 | 0.5526 | 1.033 | 0.07912 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 10 | RS11195623 | 113311380 | ADRA2A \| GPAM | INTERGENIC | G | 0.4059 | 1.013 | 0.7508 | 1.367 | 0.9314 |
| 10 | RS2900928 | 113232859 | ADRA2A \| GPAM | INTERGENIC | A | 0.4059 | 0.9779 | 0.7216 | 1.325 | 0.8852 |
| 10 | RS10509936 | 113036693 | ADRA2A \| GPAM | INTERGENIC | G | 0.4067 | 0.8501 | 0.6248 | 1.157 | 0.3013 |
| 10 | RS1360864 | 112985425 | ADRA2A \| GPAM | INTERGENIC | G | 0.4067 | 0.7508 | 0.5471 | 1.03 | 0.0759 |
| 10 | RS12218677 | 113196083 | ADRA2A \| GPAM | INTERGENIC | G | 0.4085 | 1.037 | 0.7662 | 1.403 | 0.8141 |
| 10 | RS4130310 | 113179529 | ADRA2A \| GPAM | INTERGENIC | G | 0.4085 | 1.037 | 0.7662 | 1.403 | 0.8141 |
| 10 | RS4489670 | 113181360 | ADRA2A \| GPAM | INTERGENIC | A | 0.4085 | 1.037 | 0.7662 | 1.403 | 0.8141 |
| 10 | RS7069021 | 113197606 | ADRA2A \| GPAM | INTERGENIC | G | 0.4085 | 1.037 | 0.7662 | 1.403 | 0.8141 |
| 10 | RS11599086 | 113208660 | ADRA2A \| GPAM | INTERGENIC | A | 0.4094 | 0.9583 | 0.7061 | 1.301 | 0.7845 |
| 10 | RS1832112 | 112986039 | ADRA2A \| GPAM | INTERGENIC | G | 0.411 | 0.774 | 0.5651 | 1.06 | 0.1106 |
| 10 | RS7077548 | 113360081 | ADRA2A \| GPAM | INTERGENIC | A | 0.4139 | 1.017 | 0.7532 | 1.373 | 0.9129 |
| 10 | RS4244296 | 113202840 | ADRA2A \| GPAM | INTERGENIC | G | 0.4156 | 0.9789 | 0.7233 | 1.325 | 0.8902 |
| 10 | RS1414889 | 113359740 | ADRA2A \| GPAM | INTERGENIC | A | 0.4235 | 1.053 | 0.7792 | 1.424 | 0.7356 |
| 10 | RS1914090 | 113353778 | ADRA2A \| GPAM | INTERGENIC | G | 0.4235 | 1.054 | 0.7798 | 1.425 | 0.7318 |
| 10 | RS2900934 | 113363707 | ADRA2A \| GPAM | INTERGENIC | A | 0.4245 | 1.048 | 0.7756 | 1.416 | 0.7603 |
| 10 | RS7908446 | 113406917 | ADRA2A \| GPAM | INTERGENIC | A | 0.4245 | 1.097 | 0.8132 | 1.48 | 0.5439 |
| 10 | RS10787412 | 113571480 | ADRA2A \| GPAM | INTERGENIC | G | 0.4272 | 1.145 | 0.8516 | 1.539 | 0.3704 |
| 10 | RS1923658 | 113569080 | ADRA2A \| GPAM | INTERGENIC | A | 0.429 | 1.187 | 0.8835 | 1.596 | 0.2547 |
| 10 | RS4545476 | 112922409 | ADRA2A \| GPAM | INTERGENIC | A | 0.4316 | 1.042 | 0.7642 | 1.421 | 0.7944 |
| 10 | RS10749105 | 113698172 | ADRA2A \| GPAM | INTERGENIC | A | 0.4325 | 1.253 | 0.9337 | 1.681 | 0.1328 |
| 10 | RS7083779 | 113699130 | ADRA2A \| GPAM | INTERGENIC | G | 0.4352 | 1.269 | 0.9453 | 1.704 | 0.1128 |
| 10 | RS1421057 | 113695246 | ADRA2A \| GPAM | INTERGENIC | G | 0.4395 | 1.251 | 0.9295 | 1.683 | 0.1397 |
| 10 | RS2111639 | 113696371 | ADRA2A \| GPAM | INTERGENIC | G | 0.4396 | 1.25 | 0.929 | 1.683 | 0.1405 |
| 10 | RS6585128 | 113719764 | ADRA2A \| GPAM | INTERGENIC | A | 0.444 | 0.7589 | 0.5619 | 1.025 | 0.07202 |
| 10 | RS7908674 | 112923371 | ADRA2A \| GPAM | INTERGENIC | A | 0.444 | 1.072 | 0.7864 | 1.46 | 0.6613 |
| 10 | RS2419601 | 113806381 | ADRA2A \| GPAM | INTERGENIC | G | 0.4476 | 1.134 | 0.8406 | 1.53 | 0.4102 |
| 10 | RS12766562 | 113879987 | ADRA2A \| GPAM | INTERGENIC | A | 0.4609 | 0.8814 | 0.6471 | 1.2 | 0.4232 |
| 10 | RS10885113 | 112969177 | ADRA2A \| GPAM | INTERGENIC | G | 0.4716 | 1.061 | 0.7849 | 1.434 | 0.701 |
| 10 | RS10885214 | 113333515 | ADRA2A \| GPAM | INTERGENIC | A | 0.4716 | 1.148 | 0.8481 | 1.554 | 0.3713 |
| 10 | RS4561129 | 113116998 | ADRA2A \| GPAM | INTERGENIC | A | 0.4716 | 0.9192 | 0.6851 | 1.233 | 0.5743 |
| 10 | RS608523 | 113634859 | ADRA2A \| GPAM | INTERGENIC | G | 0.4733 | 1.225 | 0.9086 | 1.651 | 0.1834 |
| 10 | RS6585131 | 113723647 | ADRA2A \| GPAM | INTERGENIC | A | 0.4733 | 1.209 | 0.8995 | 1.625 | 0.2085 |
| 10 | RS10885208 | 113309101 | ADRA2A \| GPAM | INTERGENIC | A | 0.4734 | 0.931 | 0.6879 | 1.26 | 0.6434 |
| 10 | RS2080647 | 113686345 | ADRA2A \| GPAM | INTERGENIC | A | 0.4785 | 1.228 | 0.9131 | 1.652 | 0.174 |
| 10 | RS7084370 | 113136079 | ADRA2A \| GPAM | INTERGENIC | C | 0.4805 | 0.8627 | 0.6365 | 1.169 | 0.341 |
| 10 | RS7083831 | 113135667 | ADRA2A \| GPAM | INTERGENIC | G | 0.4822 | 0.873 | 0.6451 | 1.181 | 0.3789 |
| 10 | RS3935649 | 113124810 | ADRA2A \| GPAM | INTERGENIC | G | 0.484 | 0.8693 | 0.6432 | 1.175 | 0.3621 |
| 10 | RS644420 | 113623742 | ADRA2A \| GPAM | INTERGENIC | A | 0.484 | 0.7955 | 0.5906 | 1.072 | 0.1324 |
| 10 | RS952500 | 113735304 | ADRA2A \| GPAM | INTERGENIC | G | 0.4911 | 1.267 | 0.945 | 1.699 | 0.1137 |
| 10 | RS10886416 | 120952674 | PRDX3 \| GRK5 | INTERGENIC | A | 0.1004 | 0.8071 | 0.4754 | 1.37 | 0.4275 |
| 10 | RS11198819 | 120960702 | PRDX3 \| GRK5 | INTERGENIC | G | 0.3206 | 1.247 | 0.9016 | 1.725 | 0.1823 |
| 10 | RS7923896 | 120965995 | PRDX3 \| GRK5 | INTERGENIC | G | 0.4334 | 1.115 | 0.823 | 1.51 | 0.4827 |
| 10 | RS1108472 | 120954350 | PRDX3 \| GRK5 | INTERGENIC | A | 0.4368 | 1.079 | 0.7965 | 1.461 | 0.624 |
| 10 | RS7077176 | 121146290 | GRK5 | INTRON | A | 0.05329 | 1.793 | 0.9619 | 3.342 | 0.06608 |
| 10 | RS12770361 | 121115618 | GRK5 | INTRON | A | 0.05861 | 1.298 | 0.7387 | 2.282 | 0.3641 |
| 10 | RS17606354 | 120986693 | GRK5 | INTRON | G | 0.06584 | 0.5995 | 0.2978 | 1.207 | 0.1518 |
| 10 | RS11198893 | 121107900 | GRK5 | INTRON | A | 0.07993 | 2.513 | 1.491 | 4.235 | 0.0005421 |
| 10 | RS7914808 | 121001183 | GRK5 | INTRON | A | 0.08259 | 1.01 | 0.5906 | 1.727 | 0.9709 |
| 10 | RS3740563 | 121095400 | GRK5 | INTRON | A | 0.09325 | 2.751 | 1.689 | 4.481 | 4.78E-05 |
| 10 | RS883133 | 121188960 | GRK5 | INTRON | G | 0.09769 | 1.517 | 0.9409 | 2.445 | 0.08726 |
| 10 | RS7095121 | 121149634 | GRK5 | INTRON | A | 0.1066 | 1.085 | 0.6689 | 1.759 | 0.7415 |
| 10 | RS2297641 | 121212405 | GRK5 | INTRON | A | 0.1075 | 1.632 | 1.03 | 2.585 | 0.03694 |
| 10 | RS10886477 | 121175524 | GRK5 | INTRON | A | 0.1137 | 1.355 | 0.8529 | 2.154 | 0.1983 |
| 10 | RS915110 | 121157897 | GRK5 | INTRON | A | 0.1146 | 1.312 | 0.8252 | 2.086 | 0.251 |
| 10 | RS17608274 | 121129075 | GRK5 | INTRON | A | 0.1159 | 1.169 | 0.735 | 1.858 | 0.5099 |
| 10 | RS2275044 | 121201626 | GRK5 | INTRON | A | 0.1226 | 1.181 | 0.7571 | 1.841 | 0.4639 |
| 10 | RS11195419 | 112839538 | ADRA2A | UTR | A | 0.1279 | 1.21 | 0.7713 | 1.897 | 0.407 |
| 10 | RS10886430 | 121010256 | GRK5 | INTRON | G | 0.1288 | 1.131 | 0.7431 | 1.721 | 0.566 |
| 10 | RS4752292 | 121100153 | GRK5 | INTRON | A | 0.1288 | 2.21 | 1.442 | 3.387 | 0.0002703 |
| 10 | RS2275036 | 121140321 | GRK5 | INTRON | A | 0.1306 | 0.9097 | 0.5745 | 1.44 | 0.6863 |
| 10 | RS10886464 | 121114292 | GRK5 | INTRON | A | 0.1314 | 1.885 | 1.233 | 2.881 | 0.003408 |
| 10 | RS17098857 | 121175674 | GRK5 | INTRON | A | 0.1341 | 1.183 | 0.7755 | 1.805 | 0.4351 |
| 10 | RS1556714 | 121077191 | GRK5 | INTRON | C | 0.1521 | 1.581 | 1.072 | 2.33 | 0.02072 |
| 10 | RS4237510 | 120993661 | GRK5 | INTRON | A | 0.1539 | 1.24 | 0.8351 | 1.841 | 0.2862 |
| 10 | RS10886439 | 121049565 | GRK5 | INTRON | C | 0.1643 | 0.8936 | 0.5864 | 1.362 | 0.6007 |
| 10 | RS4752276 | 121050018 | GRK5 | INTRON | G | 0.1661 | 0.8799 | 0.5774 | 1.341 | 0.5517 |
| 10 | RS7091519 | 121081794 | GRK5 | INTRON | C | 0.1901 | 1.602 | 1.117 | 2.298 | 0.01048 |
| 10 | RS11198846 | 121013417 | GRK5 | INTRON | G | 0.1918 | 0.8837 | 0.5945 | 1.313 | 0.5408 |
| 10 | RS2901211 | 121129113 | GRK5 | INTRON | G | 0.1972 | 0.7527 | 0.5066 | 1.118 | 0.1596 |
| 10 | RS291970 | 121123633 | GRK5 | INTRON | A | 0.2023 | 1.647 | 1.138 | 2.384 | 0.008209 |
| 10 | RS506657 | 121137182 | GRK5 | INTRON | A | 0.2353 | 1.552 | 1.094 | 2.202 | 0.01375 |
| 10 | RS11198906 | 121153291 | GRK5 | INTRON | A | 0.2362 | 0.8308 | 0.5758 | 1.199 | 0.3218 |
| 10 | RS1475753 | 121197945 | GRK5 | INTRON | A | 0.2442 | 1.026 | 0.7175 | 1.466 | 0.8891 |
| 10 | RS915121 | 121189480 | GRK5 | INTRON | A | 0.2469 | 1.154 | 0.8114 | 1.641 | 0.4257 |
| 10 | RS10787959 | 121131313 | GRK5 | INTRON | A | 0.2593 | 1.721 | 1.232 | 2.404 | 0.001464 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 10 | RS11198845 | 121010851 | GRK5 | INTRON | A | 0.2602 | 1.001 | 0.7111 | 1.408 | 0.9976 |
| 10 | RS17608302 | 121129167 | GRK5 | INTRON | A | 0.262 | 0.6769 | 0.471 | 0.9729 | 0.03491 |
| 10 | RS7076555 | 121180765 | GRK5 | INTRON | A | 0.27 | 0.9485 | 0.6695 | 1.344 | 0.766 |
| 10 | RS4752269 | 121037952 | GRK5 | INTRON | A | 0.278 | 1.11 | 0.8018 | 1.538 | 0.5283 |
| 10 | RS4752275 | 121049079 | GRK5 | INTRON | G | 0.2798 | 0.8846 | 0.6254 | 1.251 | 0.4885 |
| 10 | RS10886462 | 121105311 | GRK5 | INTRON | G | 0.2954 | 0.9086 | 0.6496 | 1.271 | 0.5756 |
| 10 | RS7092272 | 121106620 | GRK5 | INTRON | A | 0.302 | 0.9233 | 0.6646 | 1.283 | 0.6344 |
| 10 | RS7093673 | 120982356 | GRK5 | INTRON | A | 0.3037 | 1.165 | 0.8403 | 1.615 | 0.3597 |
| 10 | RS10886442 | 121054378 | GRK5 | INTRON | A | 0.3233 | 0.7845 | 0.5587 | 1.101 | 0.1609 |
| 10 | RS871196 | 121069074 | GRK5 | INTRON | G | 0.3339 | 0.8535 | 0.6153 | 1.184 | 0.3428 |
| 10 | RS12780837 | 121150893 | GRK5 | INTRON | A | 0.3416 | 1.091 | 0.7995 | 1.489 | 0.583 |
| 10 | RS10128498 | 121052908 | GRK5 | INTRON | G | 0.3446 | 1.051 | 0.771 | 1.433 | 0.752 |
| 10 | RS11198925 | 121197057 | GRK5 | INTRON | G | 0.3677 | 1.257 | 0.9171 | 1.722 | 0.1552 |
| 10 | RS7095989 | 121025097 | GRK5 | INTRON | C | 0.3719 | 0.8505 | 0.6203 | 1.166 | 0.3147 |
| 10 | RS915120 | 121190113 | GRK5 | INTRON | G | 0.3792 | 1.165 | 0.8527 | 1.591 | 0.3381 |
| 10 | RS6585546 | 121139331 | GRK5 | INTRON | A | 0.381 | 1.27 | 0.9293 | 1.734 | 0.1337 |
| 10 | RS4623810 | 121161798 | GRK5 | INTRON | C | 0.3837 | 1.122 | 0.8236 | 1.528 | 0.4662 |
| 10 | RS1413582 | 121132192 | GRK5 | INTRON | A | 0.3961 | 1.472 | 1.075 | 2.015 | 0.01581 |
| 10 | RS10886445 | 121062068 | GRK5 | INTRON | G | 0.4405 | 1.105 | 0.8281 | 1.474 | 0.4977 |
| 10 | RS4752263 | 120969217 | GRK5 | INTRON | A | 0.4423 | 1.112 | 0.814 | 1.519 | 0.5051 |
| 10 | RS11593107 | 121187769 | GRK5 | INTRON | G | 0.452 | 1.332 | 0.9769 | 1.817 | 0.06991 |
| 10 | RS10749321 | 121207961 | GRK5 | INTRON | A | 0.4778 | 0.6936 | 0.5037 | 0.9551 | 0.02498 |
| 10 | RS4752308 | 121184828 | GRK5 | INTRON | A | 0.4822 | 1.184 | 0.8692 | 1.613 | 0.2842 |
| 10 | RS2275040 | 121196062 | GRK5 | INTRON | G | 0.4858 | 1.373 | 1.009 | 1.87 | 0.04367 |
| 10 | RS10886471 | 121149403 | GRK5 | INTRON | G | 0.4867 | 1.122 | 0.8307 | 1.516 | 0.4526 |
| 10 | RS928670 | 121031659 | GRK5 | INTRON | G | 0.4885 | 1.054 | 0.7823 | 1.421 | 0.7287 |
| 10 | RS10510056 | 121041733 | GRK5 | INTRON | G | 0.4893 | 1.049 | 0.7783 | 1.413 | 0.7552 |
| 10 | RS4752305 | 121176601 | GRK5 | INTRON | A | 0.5 | 0.8484 | 0.6269 | 1.148 | 0.2869 |
| 10 | RS2039488 | 121244739 | GRK5 | RGS10 | INTERGENIC | G | 0.08703 | 1.596 | 0.9645 | 2.641 | 0.06887 |
| 10 | RS4751731 | 121243198 | GRK5 | RGS10 | INTERGENIC | A | 0.09414 | 1.703 | 1.044 | 2.779 | 0.03311 |
| 10 | RS4752313 | 121235040 | GRK5 | RGS10 | INTERGENIC | A | 0.09591 | 1.839 | 1.143 | 2.958 | 0.01203 |
| 10 | RS12783252 | 121232454 | GRK5 | RGS10 | INTERGENIC | A | 0.1023 | 1.385 | 0.8742 | 2.196 | 0.1652 |
| 10 | RS1999627 | 121216923 | GRK5 | RGS10 | INTERGENIC | A | 0.1066 | 1.643 | 1.037 | 2.602 | 0.03447 |
| 10 | RS10886487 | 121219038 | GRK5 | RGS10 | INTERGENIC | A | 0.1368 | 1.478 | 0.9651 | 2.265 | 0.07241 |
| 10 | RS17615995 | 121218335 | GRK5 | RGS10 | INTERGENIC | A | 0.1394 | 1.088 | 0.7059 | 1.677 | 0.702 |
| 10 | RS2901212 | 121226447 | GRK5 | RGS10 | INTERGENIC | G | 0.2043 | 1.366 | 0.9415 | 1.983 | 0.1005 |
| 10 | RS3009892 | 121249171 | GRK5 | RGS10 | INTERGENIC | A | 0.222 | 1.651 | 1.167 | 2.336 | 0.004644 |
| 10 | RS2991769 | 121231439 | GRK5 | RGS10 | INTERGENIC | G | 0.262 | 1.154 | 0.8208 | 1.623 | 0.4097 |
| 10 | RS2991770 | 121234063 | GRK5 | RGS10 | INTERGENIC | A | 0.2709 | 1.124 | 0.7966 | 1.586 | 0.5057 |
| 10 | RS11198973 | 121251611 | GRK5 | RGS10 | INTERGENIC | C | 0.322 | 1.316 | 0.9565 | 1.812 | 0.09155 |
| 10 | RS10886492 | 121225076 | GRK5 | RGS10 | INTERGENIC | A | 0.3437 | 1.444 | 1.056 | 1.975 | 0.02151 |
| 10 | RS3009874 | 121225352 | GRK5 | RGS10 | INTERGENIC | G | 0.349 | 1.469 | 1.075 | 2.008 | 0.01575 |
| 10 | RS11818431 | 113532315 | ADRA2A | GPAM | INTERGENIC | A | NA | NA | NA | NA | NA |
| 10 | RS1572444 | 113418877 | ADRA2A | GPAM | INTERGENIC | G | NA | NA | NA | NA | NA |
| 10 | RS1885652 | 113541458 | ADRA2A | GPAM | INTERGENIC | G | NA | NA | NA | NA | NA |
| 10 | RS2804613 | 113851249 | ADRA2A | GPAM | INTERGENIC | A | NA | NA | NA | NA | NA |
| 10 | RS34770130 | 115877380 | ADRB1 | C10orf118 | INTERGENIC | NA | NA | NA | NA | NA | NA |
| 10 | RS35233676 | 115806782 | ADRB1 | C10orf118 | INTERGENIC | NA | NA | NA | NA | NA | NA |
| 10 | RS7895220 | 113699501 | ADRA2A | GPAM | INTERGENIC | A | NA | NA | NA | NA | NA |
| 10 | RS679347 | 113645811 | ADRA2A | GPAM | INTERGENIC | A | 0.0008881 | 5.85E−09 | 0 | Infinite | 0.9994 |
| 10 | RS7910809 | 113762642 | ADRA2A | GPAM | INTERGENIC | G | 0.0008881 | 5.85E−09 | 0 | Infinite | 0.9994 |
| 10 | RS2419588 | 113240473 | ADRA2A | GPAM | INTERGENIC | G | 0.0008887 | 7.00E−09 | 0 | Infinite | 0.9994 |
| 10 | RS11818150 | 121070697 | GRK5 | INTRON | A | 0.001776 | 4.20E−09 | 0 | Infinite | 0.9991 |
| 10 | RS7923228 | 113053022 | ADRA2A | GPAM | INTERGENIC | G | 0.001776 | 7.43E−09 | 0 | Infinite | 0.9991 |
| 10 | RS7073650 | 113204252 | ADRA2A | GPAM | INTERGENIC | A | 0.002664 | 1.33 | 0.1186 | 14.91 | 0.8172 |
| 10 | RS7358165 | 113900251 | ADRA2A | GPAM | INTERGENIC | G | 0.003552 | 1.117 | 0.1102 | 11.32 | 0.9253 |
| 10 | RS3125480 | 113227845 | ADRA2A | GPAM | INTERGENIC | G | 0.007993 | 0.4916 | 0.059 | 4.095 | 0.5115 |
| 10 | RS17098521 | 120958585 | PDRX3 | GRK5 | INTERGENIC | A | 0.008881 | 2.108 | 0.5143 | 8.641 | 0.3001 |
| 10 | RS11198881 | 121087219 | GRK5 | INTRON | A | 0.009786 | 3.696 | 1.054 | 12.96 | 0.04107 |
| 10 | RS17129084 | 113422955 | ADRA2A | GPAM | INTERGENIC | G | 0.009786 | 2.038 | 0.5728 | 7.254 | 0.2715 |
| 10 | RS7922236 | 113440271 | ADRA2A | GPAM | INTERGENIC | A | 0.01066 | 1.749 | 0.5072 | 6.034 | 0.376 |
| 10 | RS7897542 | 113386615 | ADRA2A | GPAM | INTERGENIC | G | 0.01155 | 2.25 | 0.7078 | 7.15 | 0.1694 |
| 10 | RS7921628 | 112926122 | ADRA2A | GPAM | INTERGENIC | A | 0.01155 | 2.707 | 0.838 | 8.745 | 0.09599 |
| 10 | RS7912918 | 113077024 | ADRA2A | GPAM | INTERGENIC | A | 0.01243 | 2.63 | 0.8296 | 8.34 | 0.1005 |
| 10 | RS17098766 | 121116212 | GRK5 | INTRON | G | 0.01332 | 1.287 | 0.351 | 4.716 | 0.7037 |
| 10 | RS12242885 | 112855628 | ADRA2A | GPAM | INTERGENIC | A | 0.01421 | 1.134 | 0.308 | 4.174 | 0.8501 |
| 10 | RS9421093 | 113170248 | ADRA2A | GPAM | INTERGENIC | A | 0.01599 | 0.7965 | 0.2216 | 2.863 | 0.7273 |
| 10 | RS11195640 | 113336564 | ADRA2A | GPAM | INTERGENIC | A | 0.01776 | 1.708 | 0.587 | 4.97 | 0.3259 |
| 10 | RS2804609 | 113847037 | ADRA2A | GPAM | INTERGENIC | A | 0.01865 | 1.426 | 0.4546 | 4.471 | 0.5432 |
| 10 | RS11195815 | 113859245 | ADRA2A | GPAM | INTERGENIC | A | 0.0222 | 1.662 | 0.6645 | 4.155 | 0.2775 |
| 10 | RS12218663 | 121219756 | GRK5 | RGS10 | INTERGENIC | A | 0.02309 | 2.096 | 0.8313 | 5.287 | 0.1168 |
| 10 | RS12254157 | 113774945 | ADRA2A | GPAM | INTERGENIC | G | 0.02487 | 0.7019 | 0.2468 | 1.996 | 0.5069 |
| 10 | RS7088139 | 113390352 | ADRA2A | GPAM | INTERGENIC | A | 0.0302 | 2.05 | 0.9736 | 4.316 | 0.05884 |
| 10 | RS2804603 | 113829071 | ADRA2A | GPAM | INTERGENIC | A | 0.03108 | 1.122 | 0.4902 | 2.569 | 0.785 |
| 10 | RS2792695 | 113830311 | ADRA2A | GPAM | INTERGENIC | A | 0.03375 | 1.164 | 0.5303 | 2.554 | 0.7051 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 10 | RS4145762 | 113506321 | ADRA2A \| GPAM | INTERGENIC | A | 0.03375 | 2.013 | 0.9857 | 4.109 | 0.05481 |
| 10 | RS7895047 | 113491468 | ADRA2A \| GPAM | INTERGENIC | G | 0.03375 | 2.013 | 0.9857 | 4.109 | 0.05481 |
| 10 | RS7897951 | 113504612 | ADRA2A \| GPAM | INTERGENIC | G | 0.03375 | 2.013 | 0.9857 | 4.109 | 0.05481 |
| 10 | RS17129458 | 113757927 | ADRA2A \| GPAM | INTERGENIC | A | 0.0347 | 0.5779 | 0.2225 | 1.501 | 0.2602 |
| 10 | RS11198878 | 121082846 | GRK5 | INTRON | C | 0.03559 | 1.419 | 0.6422 | 3.138 | 0.3867 |
| 10 | RS2792709 | 113795223 | ADRA2A \| GPAM | INTERGENIC | A | 0.0373 | 1.011 | 0.4638 | 2.204 | 0.978 |
| 10 | RS2804601 | 113818913 | ADRA2A \| GPAM | INTERGENIC | A | 0.03819 | 1.004 | 0.461 | 2.184 | 0.9929 |
| 10 | RS2803594 | 113884528 | ADRA2A \| GPAM | INTERGENIC | G | 0.03908 | 0.9011 | 0.4067 | 1.997 | 0.7975 |
| 10 | RS17129380 | 113683896 | ADRA2A \| GPAM | INTERGENIC | A | 0.04263 | 1.097 | 0.557 | 2.161 | 0.789 |
| 10 | RS17129412 | 113701373 | ADRA2A \| GPAM | INTERGENIC | A | 0.04263 | 1.097 | 0.557 | 2.161 | 0.789 |
| 10 | RS1248077 | 121139045 | GRK5 | INTRON | G | 0.04707 | 0.8362 | 0.3838 | 1.822 | 0.6526 |
| 10 | RS11198978 | 121258186 | GRK5 \| RGS10 | INTERGENIC | A | 0.04796 | 1.65 | 0.8706 | 3.127 | 0.1248 |
| 10 | RS12415320 | 113592100 | ADRA2A \| GPAM | INTERGENIC | C | 0.04885 | 1.667 | 0.882 | 3.152 | 0.1156 |
| 11 | RS877711 | 74994352 | ARRB1 | CODING | A | 0.1101 | 1.05 | 0.6474 | 1.703 | 0.843 |
| 11 | RS11605263 | 67033076 | KDM2A \| ADRBK1 | INTERGENIC | A | 0.05062 | 0.9117 | 0.4434 | 1.875 | 0.8015 |
| 11 | RS1783472 | 74958948 | LOC4416171 \| ARRB1 | INTERGENIC | C | 0.07993 | 0.7752 | 0.4226 | 1.422 | 0.4107 |
| 11 | RS11236388 | 75013792 | ARRB1 | INTRON | A | 0.06774 | 0.9594 | 0.5302 | 1.736 | 0.8912 |
| 11 | RS1320709 | 74995111 | ARRB1 | INTRON | A | 0.07219 | 0.9715 | 0.5502 | 1.715 | 0.9207 |
| 11 | RS1676887 | 75019296 | ARRB1 | INTRON | A | 0.0897 | 0.6973 | 0.3867 | 1.257 | 0.2307 |
| 11 | RS685929 | 75028697 | ARRB1 | INTRON | G | 0.09609 | 1.641 | 0.9942 | 2.71 | 0.05272 |
| 11 | RS2276310 | 74982939 | ARRB1 | INTRON | A | 0.111 | 1.182 | 0.7492 | 1.865 | 0.4721 |
| 11 | RS687652 | 75022521 | ARRB1 | INTRON | G | 0.1607 | 1.143 | 0.7681 | 1.701 | 0.5097 |
| 11 | RS616714 | 75044640 | ARRB1 | INTRON | A | 0.1741 | 0.9338 | 0.626 | 1.393 | 0.7373 |
| 11 | RS746168 | 74992267 | ARRB1 | INTRON | C | 0.1918 | 0.9851 | 0.6764 | 1.435 | 0.9378 |
| 11 | RS480174 | 74995226 | ARRB1 | INTRON | A | 0.2034 | 1.061 | 0.7339 | 1.535 | 0.7518 |
| 11 | RS561923 | 75058004 | ARRB1 | INTRON | A | 0.2575 | 1.332 | 0.9543 | 1.858 | 0.09204 |
| 11 | RS566567 | 75059388 | ARRB1 | INTRON | G | 0.2584 | 1.329 | 0.9526 | 1.855 | 0.09408 |
| 11 | RS611908 | 75017087 | ARRB1 | INTRON | A | 0.2611 | 1.111 | 0.7937 | 1.554 | 0.5408 |
| 11 | RS657561 | 75020379 | ARRB1 | INTRON | A | 0.3069 | 1.013 | 0.7338 | 1.399 | 0.9371 |
| 11 | RS578130 | 75003563 | ARRB1 | INTRON | A | 0.3712 | 0.9229 | 0.6721 | 1.267 | 0.6201 |
| 11 | RS667791 | 74999428 | ARRB1 | INTRON | G | 0.3852 | 1.053 | 0.7781 | 1.425 | 0.7388 |
| 11 | RS643523 | 75041207 | ARRB1 | INTRON | G | 0.3979 | 0.6932 | 0.5031 | 0.9553 | 0.0251 |
| 11 | RS508435 | 75024816 | ARRB1 | INTRON | A | 0.4316 | 0.8906 | 0.6518 | 1.217 | 0.467 |
| 11 | RS506233 | 75012535 | ARRB1 | INTRON | G | 0.4361 | 1.246 | 0.9202 | 1.687 | 0.155 |
| 11 | RS472112 | 75021501 | ARRB1 | INTRON | G | 0.4618 | 0.9255 | 0.6817 | 1.256 | 0.6196 |
| 11 | RS2510894 | 75062178 | ARRB1 | INTRON | A | 0.4742 | 0.7177 | 0.5303 | 0.9714 | 0.03175 |
| 11 | RS536852 | 75017436 | ARRB1 | INTRON | A | 0.4885 | 0.82 | 0.6043 | 1.113 | 0.2027 |
| 11 | RS12285820 | 75080069 | ARRB1 \| RPS3 | INTERGENIC | A | 0.07815 | 0.5299 | 0.2682 | 1.047 | 0.06755 |
| 11 | RS12289289 | 75087520 | ARRB1 \| RPS3 | INTERGENIC | A | 0.08082 | 0.5584 | 0.2891 | 1.078 | 0.08273 |
| 11 | RS12271945 | 75085563 | ARRB1 \| RPS3 | INTERGENIC | A | 0.1332 | 1.153 | 0.7543 | 1.762 | 0.5107 |
| 11 | RS11236401 | 75068767 | ARRB1 \| RPS3 | INTERGENIC | G | 0.1377 | 1.074 | 0.7056 | 1.636 | 0.738 |
| 11 | RS11236414 | 75084945 | ARRB1 \| RPS3 | INTERGENIC | A | 0.2131 | 1.137 | 0.7991 | 1.619 | 0.4751 |
| 11 | RS11236410 | 75080920 | ARRB1 \| RPS3 | INTERGENIC | G | 0.214 | 1.166 | 0.8218 | 1.654 | 0.3899 |
| 11 | RS672534 | 75097031 | ARRB1 \| RPS3 | INTERGENIC | A | 0.3046 | 1.211 | 0.872 | 1.681 | 0.2534 |
| 11 | RS536516 | 75104704 | ARRB1 \| RPS3 | INTERGENIC | G | 0.4414 | 1.32 | 0.9661 | 1.803 | 0.08127 |
| 11 | RS658573 | 75075866 | ARRB1 \| RPS3 | INTERGENIC | A | 0.468 | 0.8354 | 0.6194 | 1.127 | 0.2387 |
| 11 | RS677106 | 75069871 | ARRB1 \| RPS3 | INTERGENIC | A | 0.4822 | 1.342 | 0.9995 | 1.803 | 0.05043 |
| 11 | RS582477 | 75071783 | ARRB1 \| RPS3 | INTERGENIC | C | 0.484 | 1.373 | 1.022 | 1.846 | 0.03556 |
| 11 | RS12274774 | 67046501 | ADRBK1 | INTRON | A | 0.01776 | 0.7676 | 0.2163 | 2.724 | 0.6823 |
| 17 | RS4790694 | 4626354 | ARRB2 | INTERGENIC | A | 0.1696 | 1.326 | 0.9182 | 1.914 | 0.1325 |
| 17 | RS4522461 | 4621773 | ARRB2 | INTRON | A | 0.2247 | 0.928 | 0.6443 | 1.337 | 0.6881 |
| 17 | RS3786047 | 4615098 | ARRB2 | INTRON | A | 0.2984 | 0.9958 | 0.7041 | 1.408 | 0.9809 |
| 17 | RS9905578 | 4609640 | PELP1 \| ARRB2 | INTERGENIC | A | 0.04707 | 0.8018 | 0.3826 | 1.681 | 0.5586 |
| 20 | RS6064714 | 57414140 | GNASAS \| GNAS | INTERGENIC | G | 0.1599 | 0.8069 | 0.5266 | 1.236 | 0.3244 |
| 20 | RS965808 | 57408426 | GNASAS \| GNAS | INTERGENIC | C | 0.206 | 1.027 | 0.6992 | 1.508 | 0.8927 |
| 20 | RS6092704 | 57468478 | GNAS | INTRON | C | 0.0897 | 1.577 | 0.9974 | 2.494 | 0.05132 |
| 20 | RS6026593 | 57479133 | GNAS | INTRON | G | 0.1057 | 0.9618 | 0.5942 | 1.557 | 0.8741 |
| 20 | RS6070638 | 57443831 | GNAS | INTRON | G | 0.1403 | 0.9401 | 0.6061 | 1.458 | 0.7827 |
| 20 | RS8125112 | 57431165 | GNAS | INTRON | G | 0.1643 | 0.8349 | 0.5479 | 1.272 | 0.4012 |
| 20 | RS6092708 | 57517574 | GNAS \| TH1L | INTERGENIC | A | 0.1874 | 0.8251 | 0.5461 | 1.247 | 0.3613 |
| 20 | RS11697149 | 57525478 | GNAS \| TH1L | INTERGENIC | A | 0.2401 | 0.733 | 0.5026 | 1.069 | 0.1067 |
| 20 | RS47223 | 57496873 | GNAS \| TH1L | INTERGENIC | A | 0.2922 | 1.382 | 1.001 | 1.908 | 0.04935 |
| 20 | RS234621 | 57490248 | GNAS \| TH1L | INTERGENIC | A | 0.3096 | 1.172 | 0.8535 | 1.609 | 0.3268 |
| 20 | RS3730168 | 57478939 | GNAS | INTRON | A | 0.3233 | 1.067 | 0.7769 | 1.467 | 0.6871 |
| 20 | RS13042263 | 57394925 | GNASAS \| GNAS | INTERGENIC | A | 0.3259 | 1.149 | 0.8352 | 1.581 | 0.393 |
| 20 | RS6026561 | 57427132 | GNASAS \| GNAS | INTERGENIC | G | 0.3541 | 0.731 | 0.5255 | 1.017 | 0.06265 |
| 20 | RS6026567 | 57444915 | GNAS | INTRON | G | 0.4259 | 0.9566 | 0.705 | 1.298 | 0.7755 |
| 20 | RS6026544 | 57394420 | GNASAS \| GNAS | INTERGENIC | G | 0.476 | 1.167 | 0.8568 | 1.59 | 0.3271 |
| 20 | RS919197 | 57480933 | GNAS | INTRON | A | 0.4867 | 1.033 | 0.7545 | 1.414 | 0.8394 |
| 20 | RS234613 | 57514197 | GNAS \| TH1L | INTERGENIC | G | 0.4938 | 1.06 | 0.7817 | 1.436 | 0.7092 |
| 22 | RS1001587 | 42670111 | LOC388906 | CODING | A | 0.1847 | 0.7161 | 0.4722 | 1.086 | 0.1159 |
| 22 | RS5758637 | 42580933 | TCF20 | INTRON | C | 0.2007 | 0.7712 | 0.5188 | 1.146 | 0.1989 |
| 22 | RS764481 | 42518426 | LOC100132273 \| LOC100287122 | INTERGENIC | A | 0.3099 | 1.303 | 0.9442 | 1.799 | 0.1072 |

TABLE 5-continued

A list of candidate genes and polymorphisms selected in the discovery cohort.

| Chr | SNP | Base Pair | Gene Symbol | Gene Location | Risk Allele | MAF | Odds Ratio | 95% CI LB | 95% CI UB | P-value |
|---|---|---|---|---|---|---|---|---|---|---|
| 22 | RS2413669 | 42507748 | LOC100132273 \| LOC 100287122 | INTERGENIC | C | 0.3105 | 1.296 | 0.9385 | 1.79 | 0.1153 |
| 22 | RS11090076 | 42514190 | LOC100132273 \| LOC 100287122 | INTERGENIC | G | 0.3108 | 1.295 | 0.9378 | 1.789 | 0.1164 |
| 22 | RS1801311 | 42486723 | NDUFA6 | CODING | A | 0.3108 | 1.295 | 0.9378 | 1.789 | 0.1164 |
| 22 | RS4147641 | 42482502 | NDUFA6 | INTRON | C | 0.3108 | 1.295 | 0.9378 | 1.789 | 0.1164 |
| 22 | RS134888 | 42674281 | LOC388906 \| NFAM1 | INTERGENIC | G | 0.3256 | 1.268 | 0.924 | 1.741 | 0.1414 |
| 22 | RS134901 | 42683520 | LOC388906 \| NFAM1 | INTERGENIC | G | 0.3259 | 1.273 | 0.9274 | 1.746 | 0.1355 |
| 22 | RS28439001 | 42525651 | CYP2D6 | INTRON | NA | NA | NA | NA | NA | NA |

Highlighted in gray are markers with minor allele frequency <0.05
Chr, Chromosome;
CI, confidence interval;
LB, lower boundary;
MAF, minor allele frequency;
SNP, single nucleotide polymorphism;
UB, upper boundary

TABLE 6

Genotype frequencies of the four SNPs of GRK5 in discovery and validation datasets

| | DISCOVERY DATASET (N = 563) | | VALIDATION DATASET (N = 245) | |
|---|---|---|---|---|
| GRK5 SNP | No PoAF, n = 452 (%) | Yes PoAF, n = 111 (%) | No PoAF, n = 203 (%) | Yes PoAF, n = 42 (%) |
| rs3740563 | | | | |
| CC | 369 (81.6) | 90 (81.1) | 160 (79.6) | 34 (82.9) |
| AC | 82 (18.1) | 21 (18.9) | 40 (19.9) | 7 (17.1) |
| AA | 1 (0.2) | 0 | 1 (0.5) | 0 |
| rs4752292 | | | | |
| CC | 340 (75.2) | 84 (75.7) | 140 (69.0) | (76.2) |
| AC | 108 (23.9) | 25 (22.5) | 58 (28.6) | (23.8) |
| AA | 4 (0.9) | 2 (1.8) | 5 (2.5) | 0 |
| rs11198893 | | | | |
| GG | 379 (83.8) | 94 (84.7) | 169 (83.3) | 36 (85.7) |
| AG | 73 (16.2) | 17 (15.3) | 33 (16.3) | 6 (14.3) |
| AA | 0 | 0 | 1 (4.9) | 0 |
| rs10787959 | | | | |
| GG | 249 (55.1) | 59 (53.2) | 106 (52.5) | 24 (57.1) |
| AG | 175 (38.7) | 43 (38.7) | 78 (38.6) | 16 (38.1) |
| AA | 28 (6.2) | 9 (8.1) | 18 (8.9) | 2 (4.8) |

PoAF, postoperative atrial fibrillation

What is claimed is:

1. A method of identifying and treating a subject having an increased risk of an altered effectiveness of beta blocker therapy to prevent/ameliorate postoperative atrial fibrillation during and/or after coronary artery bypass grafting surgery, comprising:
   a) obtaining a nucleic acid sample from a subject undergoing coronary artery bypass grafting surgery;
   b) detecting in the nucleic acid sample of the subject the presence of:
      i) an A allele at single nucleotide polymorphism rs3740563;
      ii) an A allele at single nucleotide polymorphism rs4752292;
      iii) an A allele at single nucleotide polymorphism rs11198893;
      iv) an A allele at single nucleotide polymorphism rs10787959; or
      v) any combination of (i) through (iv) above;
   c) identifying the subject as having an increased risk of altered effectiveness of beta blocker therapy; and
   d) administering treatment to said subject identified in step c) as having an increased risk of altered effectiveness of beta blocker therapy, wherein the treatment comprises administration of a nondihydropiridine calcium channel blocker and/or amiodarone to prevent/ameliorate postoperative atrial fibrillation, during and/or after coronary artery bypass grafting surgery.

2. The method of claim 1, wherein the detecting step consists of detecting the presence of an A allele at single nucleotide polymorphism rs3740563 and an A allele at rs4752292.

3. The method of claim 1, wherein the nondihydropiridine calcium channel blocker and/or amiodarone is administered to the subject preoperatively, perioperatively, and/or postoperatively.

4. The method of claim 1, wherein the nondihydropiridine calcium channel blocker and/or amiodarone is administered intravenously.

5. The method of claim 1, wherein the nondihydropiridine calcium channel blocker and/or amiodarone is administered to the subject perioperatively and/or postoperatively.

6. The method of claim 1, wherein the nondihydropiridine calcium channel blocker and/or amiodarone is administered to the subject postoperatively.

7. The method of claim 1, wherein the treatment comprises administration of a nondihydropiridine calcium channel blocker.

8. The method of claim 7, wherein the nondihydropiridine calcium channel blocker comprises diltiazem.

9. The method of claim 1, wherein the treatment comprises administration of amiodarone.

10. The method of claim 1, wherein the detecting comprises nucleic acid amplification and/or sequencing.

* * * * *